US008751008B2

(12) United States Patent
Carlton et al.

(10) Patent No.: US 8,751,008 B2
(45) Date of Patent: Jun. 10, 2014

(54) REMOTE CONTROL DATA MANAGEMENT WITH CORRELATION OF PATIENT CONDITION TO STIMULATION SETTINGS AND/OR WITH CLINICAL MODE PROVIDING A MISMATCH BETWEEN SETTINGS AND INTERFACE DATA

(75) Inventors: Keith Carlton, Boston, MA (US); Stephen Carcieri, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/571,119

(22) Filed: Aug. 9, 2012

(65) Prior Publication Data
US 2013/0204327 A1 Aug. 8, 2013

Related U.S. Application Data

(60) Provisional application No. 61/676,000, filed on Jul. 26, 2012, provisional application No. 61/676,014, filed on Jul. 26, 2012, provisional application No. 61/521,626, filed on Aug. 9, 2011, provisional application No. 61/521,641, filed on Aug. 9, 2011, provisional application No. 61/521,632, filed on Aug. 9, 2011.

(51) Int. Cl.
*A61N 1/08* (2006.01)
(52) U.S. Cl.
USPC .............................................. 607/59; 607/116
(58) Field of Classification Search
USPC .................................................... 607/59, 116
See application file for complete search history.

(56) References Cited

U.S. PATENT DOCUMENTS

| 5,099,846 | A | 3/1992 | Hardy |
| 5,361,763 | A | 11/1994 | Kao et al. |
| 5,452,407 | A | 9/1995 | Crook |
| 5,724,985 | A | 3/1998 | Snell et al. |
| 5,782,762 | A | 7/1998 | Vining |
| 5,938,688 | A | 8/1999 | Schiff |

(Continued)

FOREIGN PATENT DOCUMENTS

| WO | 01/90876 A1 | 11/2001 |
| WO | 2004/019799 A2 | 3/2004 |

(Continued)

OTHER PUBLICATIONS

European Patent Office, International Search Report in International Application No. PCT/US2012/050181, dated Jan. 3, 2013, 7 pages.

(Continued)

*Primary Examiner* — Christopher D Koharski
*Assistant Examiner* — Michael Carey
(74) *Attorney, Agent, or Firm* — Kenyon & Kenyon LLP

(57) ABSTRACT

A remote control device communicatively coupled to an implanted stimulation device displays representations of modifications to stimulation settings of the implanted stimulation device according to setting change instructions input by a user, without the instructed change being implemented at the implanted stimulation device. The remote control includes an input component(s) for input of patient condition information correlated to settings of the implanted stimulation device. The implanted stimulation device cycles through stimulation programs without the remote control device indicating the changes and while the remote control device receives input of patient condition information.

29 Claims, 5 Drawing Sheets

(56) References Cited

U.S. PATENT DOCUMENTS

| | | |
|---|---|---|
| 6,066,163 A | 5/2000 | John |
| 6,083,162 A | 7/2000 | Vining |
| 6,106,460 A | 8/2000 | Panescu et al. |
| 6,240,308 B1 | 5/2001 | Hardy et al. |
| 6,289,239 B1 | 9/2001 | Panescu et al. |
| 6,310,619 B1 | 10/2001 | Rice |
| 6,319,241 B1 | 11/2001 | King et al. |
| 6,351,675 B1 | 2/2002 | Tholen et al. |
| 6,389,311 B1 | 5/2002 | Whayne et al. |
| 6,463,328 B1 | 10/2002 | John |
| 6,491,699 B1 | 12/2002 | Henderson et al. |
| 6,539,263 B1 | 3/2003 | Schiff et al. |
| 6,622,048 B1 | 9/2003 | Mann et al. |
| 6,690,972 B2 | 2/2004 | Conley et al. |
| 6,694,162 B2 | 2/2004 | Hartlep |
| 6,694,163 B1 | 2/2004 | Vining |
| 6,748,098 B1 | 6/2004 | Rosenfeld |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,909,913 B2 | 6/2005 | Vining |
| 7,003,349 B1 | 2/2006 | Andersson et al. |
| 7,003,352 B1 | 2/2006 | Whitehurst |
| 7,008,370 B2 | 3/2006 | Tanner et al. |
| 7,035,690 B2 | 4/2006 | Goetz |
| 7,043,293 B1 | 5/2006 | Baura |
| 7,050,857 B2 | 5/2006 | Samuelsson et al. |
| 7,107,102 B2 | 9/2006 | Daignault, Jr. et al. |
| 7,136,518 B2 | 11/2006 | Griffin et al. |
| 7,136,695 B2 | 11/2006 | Pless et al. |
| 7,146,219 B2 | 12/2006 | Sieracki et al. |
| 7,146,223 B1 | 12/2006 | King |
| 7,151,961 B1 | 12/2006 | Whitehurst et al. |
| 7,155,279 B2 | 12/2006 | Whitehurst et al. |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,209,787 B2 | 4/2007 | DiLorenzo |
| 7,216,000 B2 | 5/2007 | Sieracki et al. |
| 7,217,276 B2 | 5/2007 | Henderson et al. |
| 7,218,968 B2 | 5/2007 | Condie et al. |
| 7,231,254 B2 | 6/2007 | DiLorenzo |
| 7,239,910 B2 | 7/2007 | Tanner |
| 7,239,926 B2 | 7/2007 | Goetz |
| 7,242,984 B2 | 7/2007 | DiLorenzo |
| 7,252,090 B2 | 8/2007 | Goetz |
| 7,254,446 B1 | 8/2007 | Erickson et al. |
| 7,257,447 B2 | 8/2007 | Cates et al. |
| 7,266,412 B2 | 9/2007 | Stypulkowski |
| 7,295,876 B1 | 11/2007 | Erickson |
| 7,313,430 B2 | 12/2007 | Urquhart et al. |
| 7,324,851 B1 | 1/2008 | DiLorenzo |
| 7,346,382 B2 | 3/2008 | McIntyre et al. |
| 7,388,974 B2 | 6/2008 | Yanagita |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,603,177 B2 | 10/2009 | Sieracki et al. |
| 7,617,002 B2 | 11/2009 | Goetz |
| 7,623,918 B2 | 11/2009 | Goetz |
| 7,657,319 B2 | 2/2010 | Goetz et al. |
| 7,676,273 B2 | 3/2010 | Goetz et al. |
| 7,826,902 B2 | 11/2010 | Stone et al. |
| 7,848,802 B2 | 12/2010 | Goetz et al. |
| 2004/0034394 A1 | 2/2004 | Woods et al. |
| 2004/0044279 A1 | 3/2004 | Lewin et al. |
| 2004/0106916 A1 | 6/2004 | Quaid et al. |
| 2004/0199216 A1 | 10/2004 | Lee et al. |
| 2004/0267330 A1 | 12/2004 | Lee et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0171587 A1 | 8/2005 | Daglow et al. |
| 2006/0017749 A1 | 1/2006 | McIntyre et al. |
| 2006/0020292 A1 | 1/2006 | Goetz et al. |
| 2006/0094951 A1 | 5/2006 | Dean et al. |
| 2006/0235472 A1 | 10/2006 | Goetz et al. |
| 2006/0259079 A1 | 11/2006 | King |
| 2007/0017749 A1 | 1/2007 | Dold et al. |
| 2007/0043268 A1 | 2/2007 | Russell |
| 2007/0049817 A1 | 3/2007 | Preiss et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0156186 A1 | 7/2007 | Lee et al. |
| 2007/0162086 A1 | 7/2007 | DiLorenzo |
| 2007/0185544 A1 | 8/2007 | Dawant et al. |
| 2007/0191912 A1 | 8/2007 | Fischer et al. |
| 2007/0203450 A1 | 8/2007 | Berry |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1* | 8/2007 | Goetz et al. ............. 607/59 |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0071150 A1 | 3/2008 | Miesel et al. |
| 2008/0081982 A1 | 4/2008 | Simon et al. |
| 2008/0103533 A1 | 5/2008 | Patel et al. |
| 2008/0123922 A1 | 5/2008 | Gielen et al. |
| 2008/0141217 A1 | 6/2008 | Goetz et al. |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0215118 A1 | 9/2008 | Goetz et al. |
| 2008/0269588 A1 | 10/2008 | Csavoy et al. |
| 2008/0300654 A1* | 12/2008 | Lambert et al. ............. 607/59 |
| 2009/0082640 A1* | 3/2009 | Kovach et al. ............. 600/300 |
| 2009/0082829 A1 | 3/2009 | Panken et al. |
| 2009/0112289 A1 | 4/2009 | Lee et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1* | 8/2009 | Goetz et al. ............. 607/59 |
| 2009/0204192 A1 | 8/2009 | Carlton et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010646 A1 | 1/2010 | Drew et al. |
| 2010/0023130 A1 | 1/2010 | Henry et al. |
| 2010/0049276 A1 | 2/2010 | Blum et al. |
| 2010/0049280 A1 | 2/2010 | Goetz |
| 2011/0191275 A1 | 8/2011 | Lujan et al. |

FOREIGN PATENT DOCUMENTS

| | | |
|---|---|---|
| WO | 2007/097859 A1 | 8/2007 |
| WO | 2007/097861 A1 | 8/2007 |
| WO | 2007/100427 A1 | 9/2007 |
| WO | 2007/100428 A1 | 9/2007 |
| WO | 2007/112061 A2 | 10/2007 |

(56) References Cited

FOREIGN PATENT DOCUMENTS

| | | |
|---|---|---|
| WO | 2010/120823 A2 | 10/2010 |
| WO | 2011/139779 A1 | 11/2011 |
| WO | 2011/159688 A2 | 12/2011 |

OTHER PUBLICATIONS

Butson et al., "Current Steering to Control the Volume of Tissue Activated During Deep Brain Stimulation," Brain Stimulation 1, 2008, pp. 7-15.

Butson et al., "Patient-Specific Analysis of the Volume of Tissue Activated During Deep Brain Stimulation," Neuroimage 34, 2007, pp. 661-670.

Butson et al., "Role of Electrode Design on the Volume of Tissue Activated During Deep Brain Stimulation," Journal of Neural Engineering, Mar. 1, 2006, vol. 3, No. 1, pp. 1-8.

Butson et al., "StimExplorer: Deep Brain Stimulation Parameter Selection Software System," Acta Neurochirugica, Jan. 1, 2007, vol. 97, No. 2, pp. 569-574.

Miocinovic et al., "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Schmidt et al., "Sketching and Composing Widgets for 3D Manipulation," Eurographics, Apr. 2008, vol. 27, No. 2, pp. 301-310.

Izad, Olivier, "Computationally Efficient Method in Predicating Axonal Excitation," Dissertation for Masters Degree, Department of Biomedical Engineering, Case Western Reserve University, May 2009, 144 pages.

Jaccard, Paul, "Étude comparative de la distribution florale dans une portion odes Aples et des Jura," Bulletin de la Société Vaudoise des Sciences Naturelles (1901), vol. 37, pp. 547-579.

Dice, Lee R., "Measures of the Amount of Ecologic Association Between Species," Ecology 26(3) (1945), pp. 297-302. doi:10.2307/1932409, http://jstor.org/stable/1932409.

Rand, W.M., "Objective criteria for the evaluation of clustering methods," Journal of the American Statistical Association (American Statistical Association) 66 (336) (1971), pp. 846-850, doi:10.230712284239, http://jstor.org/stable/2284239.

Hubert, Lawrence et al., "Comparing partitions," Journal of Classification 2(1) (1985), pp. 193-218, doi:10.1007/BF01908075.

Cover, T.M. et al., "Elements of information theory," (1991) John Wiley & Sons, New York, NY, pp. 1-542.

Meila, Marina, "Comparing Clusterings by the Variation of Information," Learning Theory and Kernel Machines (2003), pp. 173-187.

European Patent Office, International Search Report in International Application No. PCT/US2012/053344, dated Nov. 26, 2012, 8 pages.

European Patent Office, International Search Report and the Written Opinion of the International Searching Authority in International Application No. PCT/US20121050175, dated Oct. 26, 2012, 15 pages.

European Patent Office, International Search Report and Written Opinion in International Application No. PCT/US2012/030700, dated Feb. 27, 2013, 9 pages.

Euopean Patent Office, International Search Report and the Written Opinion in International Application No. PCT/US2012/050170, dated Oct. 5, 2012, 15 pages.

Ericsson, A. et al., "Construction of a patient-specific atlas of the brain: Application to normal aging," Biomedical Imaging: From Nano to Macro, ISBI 2008, 5th IEEE International Symposium, 14 May 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al, "Assessing selection methods in the context of multi-atlas based segmentation," Biomedical Imaging: From Nano to Macro, 2010 IEEE International Symposium, 14 Apr. 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al, "Fast and robust multi-atlas segmentation of brain magnetic resonance images," NeuroImage, Academic Press, vol. 49, No. 3, Feb. 1, 2010, pp. 2352-2365.

European Patent Office, PCT Search Report from PCT/US09/03041, dated Aug. 20, 2009, 7 pages.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

European Patent Office, PCT Search Report from PCT/US09/03017, dated Aug. 3, 2009, 7 pages.

European Patent Office, PCT Search Report from PCT/US09/03038, dated Oct. 8, 2009, 9 pages.

European Patent Office, PCT Search Report from PCT/US09/03040, dated Aug. 13, 2009, 7 pages.

European Patent Office, PCT Search Report from PCT/US09/03049, dated Jan. 26, 2010, 8 pages.

European Patent Office, partial International Search Report in International Application No. PCT/US2012/030701, dated Feb. 15, 2013, 7 pages.

European Patent Office, partial International Search Report in International Application No. PCT/US2012/030705, dated Mar. 6, 2013, 7 pages.

European Patent Office, International Search Report and Written Opinion in International Application No. PCT/US2012/050187, dated Feb. 27, 2013, 9 pages.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

European Patent Office, International Search report and Written Opinion in PCT application No. PCT/US12/50174, dated Mar. 6, 2013, 20 pages.

\* cited by examiner

REMOTE CONTROL DATA MANAGEMENT WITH CORRELATION OF PATIENT CONDITION TO STIMULATION SETTINGS AND/OR WITH CLINICAL MODE PROVIDING A MISMATCH BETWEEN SETTINGS AND INTERFACE DATA

CROSS-REFERENCE TO RELATED APPLICATIONS

The present application claims priority to U.S. Provisional Patent Application Ser. Nos. 61/521,626 filed on Aug. 9, 2011, 61/521,641 filed on Aug. 9, 2011, 61/521,632 filed on Aug. 9, 2011, 61/676,000 filed on Jul. 26, 2012 and 61/676,014 filed on Jul. 26, 2012, the content of all of which is hereby incorporated by reference herein in their entireties.

FIELD OF THE INVENTION

Aspects of the present invention pertain to management of data in a central location for access at multiple locations, by various machines, and via various applications. Aspects of the present invention pertain to an interface of a stimulation setting remote control in a clinical mode. Aspects of the present invention pertain to sharing of target volumes of activation. The applications and systems via which the various data is created and/or accessed and/or used and/or in which the described interfaces may be presented may include any one of those described in U.S. patent application Ser. No. 12/454,330, filed May 15, 2009 ("the '330 application") which published as U.S. Pat. App. Pub. No. 2009/0287271, U.S. patent application Ser. No. 12/454,312, filed May 15, 2009 ("the '312 application") which issued as U.S. Pat. No. 8,326,433, U.S. patent application Ser. No. 12/454,340, filed May 15, 2009 ("the '340 application") which published as U.S. Pat. App. Pub. No. 2009/0287272, U.S. patent application Ser. No. 12/454,343, filed May 15, 2009 ("the '343 application") which published as U.S. Pat. App. Pub. No. U.S. patent application Ser. No. 12/454,314, filed May 15, 2009 ("the '314 application") which published as U.S. Pat. App. Pub. No. 2009/0287467, U.S. Provisional Pat. App. Ser. No. 61/468,884, filed Mar. 29, 2011 ("the '884 application"), U.S. Provisional Pat. App. Ser. No. 61/468,887, filed Mar. 29, 2011 ("the '887 application"), U.S. Provisional Pat. App. Ser. No. 61/468,891, filed Mar. 29, 2011 ("the '891 application"), U.S. Provisional Pat. App. Ser. No. 61/468,897, filed Mar. 29, 2011 ("the '897 application"), and U.S. Provisional Pat. App. Ser. No. 61/468,901, filed Mar. 29, 2011 ("the '901 application"), the content of each of which is hereby incorporated herein by reference in its entirety.

BACKGROUND INFORMATION

Electrical stimulation of an anatomical region, e.g., deep brain stimulation (DBS), such as of the thalamus or basal ganglia, is a clinical technique for the treatment of disorders such as essential tremor, Parkinson's disease (PD), and other physiological disorders. DBS may also be useful for traumatic brain injury and stroke. Pilot studies have also begun to examine the utility of DBS for treating dystonia, epilepsy, and obsessive-compulsive disorder.

A stimulation procedure, such as DBS, typically involves first obtaining preoperative images, e.g., of the patient's brain, such as by using a computed tomography (CT) scanner device, a magnetic resonance imaging (MRI) device, or any other imaging modality. This sometimes involves first affixing to the patient's skull spherical or other fiducial markers that are visible on the images produced by the imaging modality. The fiducial markers help register the preoperative images to the actual physical position of the patient in the operating room during the later surgical procedure.

After the preoperative images are acquired by the imaging modality, they are then loaded onto an image-guided surgical (IGS) workstation, and, using the preoperative images displayed on the IGS workstation, a neurosurgeon can select a target region, e.g., within the brain, an entry point, e.g., on the patient's skull, and a desired trajectory between the entry point and the target region. The entry point and trajectory are typically carefully selected to avoid intersecting or otherwise damaging certain nearby critical structures or vasculature, e.g., of the brain.

In the operating room, the physician marks the entry point on the patient's skull, drills a burr hole at that location, and affixes a trajectory guide device about the burr hole. The trajectory guide device includes a bore that can be aimed to obtain the desired trajectory to the target region. After aiming, the trajectory guide is locked to preserve the aimed trajectory toward the target region. After the aimed trajectory has been locked in using the trajectory guide, a microdrive introducer is used to insert the surgical instrument along the trajectory toward the target region, e.g., of the brain. The surgical instrument may include, among other things, a recording electrode leadwire, for recording intrinsic electrical signals, e.g., of the brain; a stimulation electrode leadwire, for providing electrical energy to the target region, e.g., of the brain; or associated auxiliary guidewires or guide catheters for steering a primary instrument toward the target region, e.g., of the brain.

The stimulation electrode leadwire, which typically includes multiple closely-spaced electrically independent stimulation electrode contacts, is then introduced to deliver the therapeutic stimulation to the target region, e.g., of the brain. The stimulation electrode leadwire is then immobilized, such as by using an instrument immobilization device located at the burr hole entry, e.g., in the patient's skull, in order for the DBS therapy to be subsequently performed.

The subthalamic nucleus (STN) represents the most common target for DBS technology. Clinically effective STN DBS for PD has typically used electrode contacts in the anterior-dorsal STN. However, STN DBS exhibits a low threshold for certain undesirable side effects, such as tetanic muscle contraction, speech disturbance and ocular deviation. Highly anisotropic fiber tracks are located about the STN. Such nerve tracks exhibit high electrical conductivity in a particular direction. Activation of these tracks has been implicated in many of the DBS side effects. However, there exists a limited understanding of the neural response to DBS. The three-dimensional (3-D) tissue medium near the DBS electrode typically includes both inhomogeneous and anisotropic characteristics. Such complexity makes it difficult to predict the particular volume of tissue influenced by DBS.

After the immobilization of the stimulation electrode leadwire, the actual stimulation therapy is often not initiated until after a time period of about two-weeks to one month has elapsed. This is due primarily to the acute reaction of the brain tissue to the introduced electrode leadwire (e.g., the formation of adjacent scar tissue), and stabilization of the patient's disease symptoms. At that time, a particular one or more of the stimulation electrode contacts is selected for delivering the therapeutic stimulation, and other stimulation parameters are adjusted to achieve an acceptable level of therapeutic benefit.

A system and method may estimate stimulation volumes, and display models of a patient anatomy and/or a stimulation leadwire, via which to graphically identify the estimated stimulation volumes and how they interact with various regions of the patient anatomy, for example, as described in the '330, '312, '340, '343, and '314 applications.

The systems and methods may be used to explore target regions of stimulation and stimulation therapies to determine which therapy regimen is best suited for a particular patient or group of patients.

SUMMARY

Such exploration may result in much data over time for a particular patient and/or for a patient population. Example embodiments of the present invention provide a system and methods to improve the quality of such data, to manage such data, and to maximize use of, and facilitate efficient use of, such information.

The data may pertain to, for example, stimulation of a patient for deep brain stimulation (DBS) therapy and/or spinal cord stimulation (SCS) therapy. It may include graphical information, such as estimated volumes of activation (VOA), also referred to herein as a stimulation field model (SFM). It may include information used for rendering the SFMs, such as image registration and/or leadwire location data. It may further include information regarding the patient's condition, such as disease and medications taken, and/or reactions to an applied therapy. It may further include information concerning stimulation programs applied to the patient for the patient therapy. It may include target volumes selected for a patient, and/or volumes of estimated activation (VOA) for various stimulation parameters input for the patient. It may include information concerning how close the patient's anatomical images match to a standard atlas. It may further include analytics information as described below.

Various systems, system components, and/or program modules may be used for performance of various tasks associated with, or that provide an output usable for, providing therapeutic stimulation, generation of data regarding a therapy, and access to and transfer of therapy data. Embodiments of the present invention provide for communication and/or between the various systems, system components, and/or program modules.

The various methods described herein may be practiced, each alone, or in various combinations.

An example embodiment of the present invention is directed to a processor, which may be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. In certain example embodiments, the processor may be embodied in a remote control device. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to a hardware computer-readable medium, e.g., as described above, having stored thereon instructions executable by a processor to perform the methods described herein.

An example embodiment of the present invention is directed to a method, e.g., of a hardware component or machine, of transmitting instructions executable by a processor to perform the methods described herein.

DETAILED DESCRIPTION

Cloud Data Management

Figure 1:
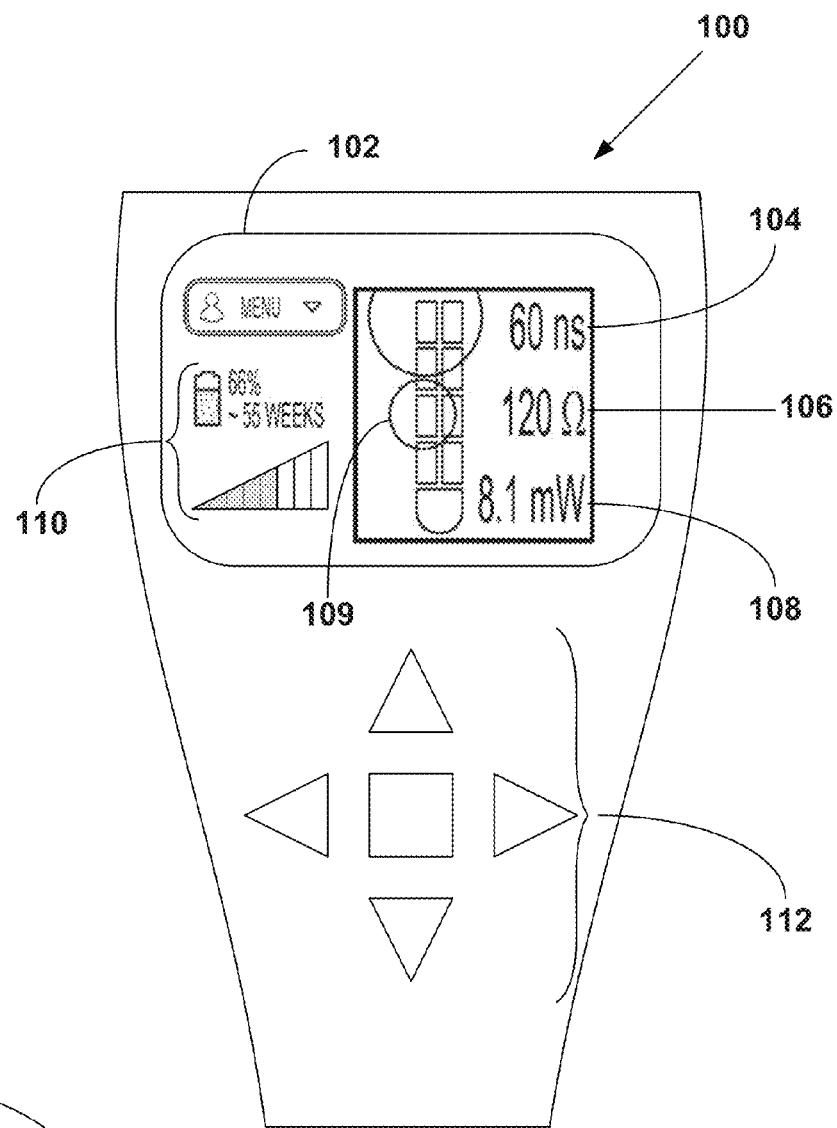
FIG. 1 illustrates a remote control device according to an example embodiment of the present invention.

A Guide software for stimulation therapy may require various data used at various points of time. Example embodiments of the present invention provide for getting the information to go to the right place at the right time. Additionally, example embodiments allow for patient data to travel with the patient. Information may include the graphics, but may also include other non-imagery data, as noted above, such as side effects, tremors (e.g., measured by an accelerometer in the implantable pulse generator (IPG)), medications, and other clinical data that would have to be updated over time.

In an example embodiment of the present invention, a patient can be assigned and given an identification (ID) card that has the patient's data. For example, the card may be inserted into, or otherwise be provided in communication with, a computer and data on the computer may be recorded on the card. However, as explained in connection with the alternative embodiments below, the data need not be stored on the card, and the card would then only be used for obtaining access to the data, which can be stored remotely in a central server.

In an alternative example embodiment, the patient has a card that includes a pin number that one can use to access the patient's information.

In an alternative example embodiment, the patient has a card that includes an account number that, when input to a computer along with a pin number from the user's memory, allows access to the patient's information.

In an alternative example embodiment, the card includes a number that, when the card is swiped in a device connected to a computer, is read by the computer, and that thereby allows access to the data of the patient associated with the number. In an example embodiment, the number can be one on the patient's implanted IPG, which is already managed to have unique numbers. Use of such a number, rather than patient name, can help with anonymization issues. That is, the data is stored in connection with a number, rather than in association with data by which can identify the patient.

A problem is where data is recorded before the user obtains the IPG. In this instance, a temporary number may be assigned, and then, when the IPG is implanted, a switchover may be made to the number of the IPG.

Use of the IPG number may be advantageous because even if the user loses the card, the user can obtain the information by using the IPG which obviously does not get lost.

In an example embodiment of the present information the IPG may transmit a signal with the number. According to this embodiment, the card may be omitted. Instead, the signal of the IPG indicating the unique number (or any unique signal that may be omitted by the IPG which unique signal is associated with the particular patient) may allow the data access. Not only the IPG, but any RFID device provided to the user can be used to provide the number. However, it is preferred to use a device implanted in the patient, so that it is ensured not to be lost.

The computer may "talk" to the signaling device on the patient to get the number needed to obtain (or send to the server) the information. For example, the user may connect a device to a port of a computer (e.g., a USB port, a serial port or any other communications port), which device is configured to receive a signal from the IPG, which indicates some number. The number is sent to the central server and then the information is obtained. This can be great for security as well because it allows the system to be controlled not to send the information unless the device recognizes that the patient with the correct IPG is physically present at the computer terminal at which the information is being requested or via which information is being stored.

The guide system, including the visualization package, the clinician programmer (CP) by which the clinician actually sets the IPG, or the patient programmer system by which the IPG settings can be changed without the clinician, and the analytic system (described below) can each access the information in the cloud. In an example embodiment, any web browser may be used to access the information.

Different users can have different types of access. For example, a patient may have a certain level of access, a health care provider may have another level of access, and a relative (who is not the health care provider) can have yet another level of access.

In an example embodiment, the IPG may be programmed to generate, based on a user-input code, a second code that provides a specific level of access. The second code may be unique to the user (e.g., a particular health care provider). In this manner, different levels of access may be provided to data generated using the same IPG. Thus, for example, a health care provider may only be able to access IPG data generated at the provider's facility, but may not have access to IPG data generated at other provider facilities, even though the IPG is the same.

In an example embodiment, health care providers may be provided with the ability to access the data without the patient (and therefore the IPG) being physically present. For example, the provider may store the patient's access credentials (e.g., IPG number) the first time the patient visits, so that patient data can be obtained prior to the next visit.

Additional data that can be included in the central location for access as described above is analytics information as described below and the data used for the analytics.

Additional information stored in the cloud can be logs of the changes entered by the patients to their parameters using the remote control, which changes would be time-stamped, as described below. The remote control will record the information. The remote control can be plugged into a computer which then sends it to the central location for storage in association with the number that is unique to the patient. Alternatively, it can be sent continuously or periodically through, e.g., a wireless connection, e.g., via a cellular connection. Alternatively, the remote control can connect to a device through a wireless connection, and, when so connected, it can send the information to the central server.

Additionally, the detailed computations—fusion of MR/CT, fusion of atlas to MR, lead location, VOA generation, etc. (see all computations and data described in the '330, '312, '340, '343, '314, '884, '887, '891, '897, and '901 applications)—can be performed at a server and the resulting information can be stored centrally.

In an example embodiment, transformation matrix parameters can be stored centrally. For example, the central server, the IPG, and/or the remote used by the patient would store the transformation matrices, such as how to transform the atlas to the patient's MR. Additionally, it would store the location of the lead in the resulting patient-specific atlas. It would also store an atlas identifier to identify which atlas is the one being transformed, in case different atlases are used at different times, e.g., because of a software upgrade.

Data Export/Import

According to an example embodiment of the present invention, a same stimulation-related and/or anatomical atlas (patient-specific or non-patient-specific) data can be accessed via multiple computer terminals. For example, in an example embodiment, such data is saved to a file stored at a central location accessible from multiple computer terminals.

In an example embodiment of the present invention, such data can be shared with other users, e.g., as an attachment to a communication (e.g., an e-mail) or by providing the other user access to the centrally stored file. Such data often includes information that is specific to a patient and private. Accordingly, in an example embodiment of the present invention, the system includes an anonymization feature for stripping from the shared data any data that identifies the patients. For example, in an example embodiment, the system includes a soft or hard selectable button, in response to selection of which the system strips private data. For example, the system can be programmed to remove patient name, address, social security, etc. In an example embodiment, in response to selection of the anonymization button, the system outputs a list of types of data which the user can select to strip. In an alternative example embodiment, the system saves the information centrally with all of the data, and depending on permissions set for a user attempting to access the centrally stored data, either provides the data with the private information or provides a stripped-down version of the data.

According to an example embodiment of the present invention, the system is configured to transmit VOAs or other volumes in the form of centroids (e.g., center of mass of the volume), e.g., in combination with other elliptically based information, as further described below. In an example embodiment, volumes can be transmitted/opened in a CAD format. Volumes can be exported to other users in the reference frame of the patient for whom the volume was generated. Alternatively, the volume can be transformed to a common reference frame, e.g., a common atlas, and transmitted to other users in this generic form. In an example embodiment, the system is configured to export the VOA or other volume as a full 3D mesh of the volume.

In an example embodiment, the system is configured to export geometric primitives of the volumes, e.g., of the VOAs. For example, in an example embodiment, the system saves/transmits the parameters of a sphere or ellipse that best matches the VOA, which allows for the amount of data that is to be saved and/or exported to be scaled down. Such data can be sent, for example, in an Excel format, as comma delimited file, as text file, or as a CAD file. Providing the volume information in such forms can be beneficial to allow one to use third party applications not adapted to interpret/process the more intricate volume data the Guide software is configured to process.

For example, a volume, e.g., a VOA, can be saved/transmitted as a set of points in 3D space with information on how those points are connected. Alternatively, the volume can be saved as a combination of a centroid and, for example, a radius. The radius can be that which is determined to provide an ellipse that optimally overlaps the volume, e.g., with least combined difference of overlap and underlap to the volume or the smallest ellipse that covers all points of the volume. For example, the system can store a plurality of volumes, each as a row including the data $\{x, y, z, r\}$, where x, y, z represent a point in three-dimensional space at a center of mass of the volume and r represents the radius.

Figure 9:
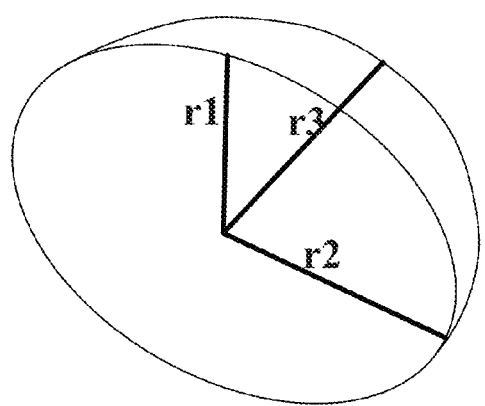
FIG. 9 illustrates components usable for representing an anatomical volume, according to an example embodiment of the present invention.

According to a variant of this embodiment, the system can include multiple radii to represent the volume, for example, to represent a three-dimensional ellipsoid. For example, three radii can be used, each for a respective one of the x, y, and z directions, as shown in FIG. 9. In an example embodiment of the present invention, the system further provides additional data indicating an orientation of the ellipse in an atlas or anatomical image space. This is because the same ellipse can be orientated in a number of ways relative to the same anatomical space. In an example embodiment of the present invention, the orientation information is provided as any two of three angles. For example, a first angle can represent an angular offset from the superior-inferior line, a second angle can represent an offset from the anterior-posterior line, and a third angle can represent an offset from the medial-lateral line. Thus, each of the radii can be a radius drawn along one of those lines, and each angle can be a respective offset for a respective one of those radii.

Alternatively, geometric primitives other than radii and/or x,y,z coordinates can be used as an estimate of the volume. For example, a geometric primitive to be used for characterizing a sphere can be a diameter; geometric primitives to be used for characterizing an ellipsoid can be axes lengths; geometric primitives to be used for characterizing a hexagon can be side lengths; geometric primitives to be used for characterizing a pyramid can be a height, lower radius, upper radius, etc.

Other data can be provided to further define the volumes, e.g., warping parameters, such as an indication of an amount of warp, a direction of warp, etc.

In an example embodiment, a geometric volume can be represented by identification of elements, voxels, or nodes that are included or excluded, e.g., the system includes a standard format by which to present such information.

In an example embodiment of the present invention, a more precise volume can be saved/transmitted in an Excel, comma delimited, or other similar format. For example, in an example embodiment, a volume can be represented using a first record corresponding to a volume includes a plurality of tuples, each tuple corresponding to a single point in two or three dimensional space, and a second record identifying each pair or triple of connected ones of the points. For example, the following record can be stored $\{x_1, y_1, z_1; x_2, y_2, z_2; x_3, y_3, z_3; \ldots\}$, where each x, y, z, combination is one point on a perimeter of the volume. The following additional record can be stored $\{1, 2, 3; 3, 4, 5; \ldots\}$, where each combination of numbers identifies a respective combination of tuples that are connected. For example, "1, 2, 3" indicates that the point of tuple 1 is connected to the point of tuple 2 and to the point of tuple 3. If points of a two-dimensional volume are stored/transmitted, the second record may be in the form of, for example, $\{1, 2; 2, 3; 3, 4; \ldots\}$, where each combination of numbers identifies a respective combination of tuples that are connected. For example, "1, 2" indicates that the point of tuple 1 is connected to the point of tuple 2, etc.

Data Capture on the Remote Control (Patient Programmer)

A need in neuromodulation is to have some way to blind a patient as to whether the patient's device is on or off. This is helpful, for example, for clinical trials. This is difficult because the patient usually has a remote control that informs the patient of this information. Therefore, according to an example embodiment of the present invention, the remote control is provided with a clinical mode, where the remote creates the illusion as though the device is on, e.g., the user can interact with a user interface to raise or lower the stimulation amplitude and/or other settings, when really nothing is happening in response, although the remote gives the appearance as though the system is responding to the user's commands.

For example, referring to FIG. 1, a remote control 100 can include a display screen 102 including graphical information regarding parameters set in the IPG, including, for example, the pulse width 104, current amplitude 106, and power amplitude 108 of electrodes of an implanted leadwire controlled by the IPG. The display screen 102 can include additional information regarding the IPG, such as one or more representations of its battery power and life 110. The remote control 100 can include one or more buttons 112 via which the patient can input instructions to the IPG for modifying one or more of the settings. For example, the user can, in an example embodiment, select an electrode and input a desired amplitude setting, polarity, etc. for the selected electrode, e.g., by textual input, or by selecting an up or down arrow to raise or lower a setting. In an example embodiment, a graphical representation of an electric field 109 drawn about one or more graphical representations of respective electrodes can be shifted, e.g., using arrow keys, which is interpreted as an instruction to modify one or more settings to provide the shifted electric field. The remote control 100 can include other features for input of stimulation settings, for example, as described in the '330, '312, '340, '343, and '314 applications.

In an example embodiment, when the remote control 100 is in the clinical mode, if the user manipulates the input elements, e.g., buttons 112, of the remote control 100 to modify the settings of the IPG, the remote control 100 updates the graphical user interface (GUI) to reflect the input modifications, without the input modification instruction being implemented at the IPG. For example, the remote control 100 can refrain from responsively transmitting modification instructions to the IPG, or the remote control 100 can transmit the instruction, but the IPG can ignore the instruction. According to the latter embodiment, the IPG enters the clinical mode, while the remote control 100 is blind to whether the system is in a clinical or a regular mode. Although the instruction to modify the settings is not executed, the remote control 100 can display the modified setting, such as a modified pulse width, current amplitude, and/or power setting, and/or the location(s) of one or more of the displayed current fields, as though it had been implemented.

The remote control 100 can also modify the battery power and life representations 110 to reflect the modifications as though they had been implemented. For example, in response to instructions for modifications that when implemented would cause a change in the battery power and expected battery life, the remote control 100 may update the battery power and life representations to reflect such change, although the modifications are not implemented.

Additionally, in an example embodiment, where the IPG does not perform with the leadwire a stimulation, such that battery power of the IPG is not being used or is used at a very low rate, but the patient is led to believe in clinical mode that a stimulation program is being applied, the remote control 100 modifies the battery power and life representations 110 as though the stimulation program is being applied.

In an example embodiment of the present invention, in the clinical mode, the remote control 100 provides an output, e.g., a graphical, audible, or tactile output, warning of low battery power of the IPG, such that a recharge is suggested, in accordance with the indicated stimulation program, although the program is not being applied and the battery power is in fact not depleted.

In an example embodiment, the remote control 100 includes a charger for charging the IPG battery. For example, the remote control 100 can include a wire with a coil for inductively charging the IPG. In the clinical mode, where the IPG battery is shown to be at less than its actual charge level, and the user uses the remote control 100 in order to charge the IPG battery (although the battery might be fully charged), the remote control 100 may update the battery power and life representations 110 to reflect an increase in the battery power and remaining life, as though being increased from the low battery power and life indications.

Figure 2:
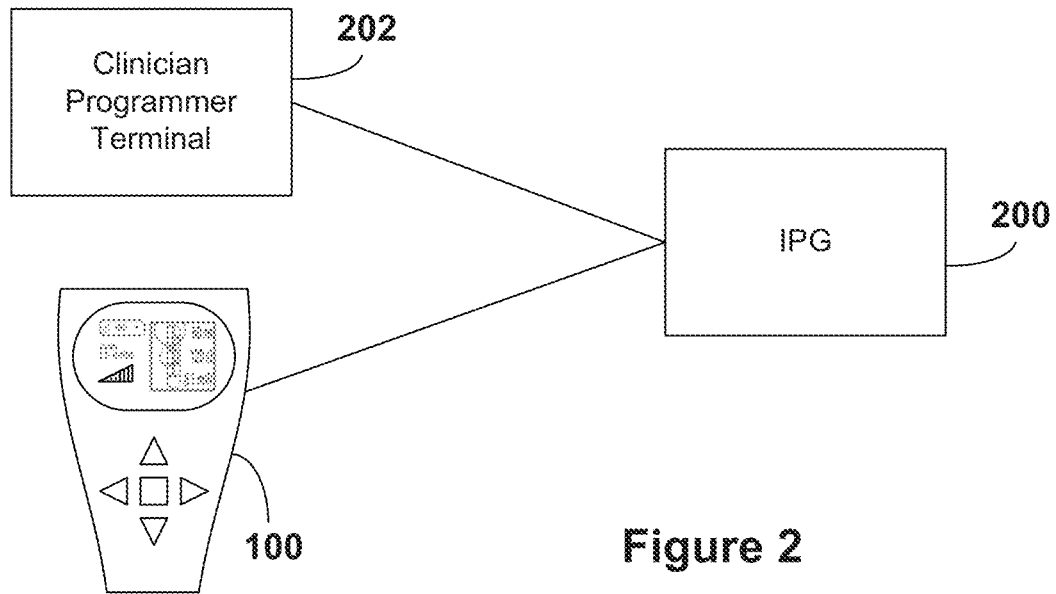
FIG. 2 shows connections between a remote control device and other system components according to an example embodiment of the present invention.

In an example embodiment of the present invention, as shown in FIG. 2, the remote control 100 communicates with the IPG 200 and also interacts with a CP terminal 202, e.g., a laptop or other computer terminal in which a clinician programmer application is executed.

For example, a user operating the CP terminal 202 can input upper and/or lower bounds of a parameter of the IPG 200, e.g., upper and lower amplitudes for a stimulation program. The CP terminal 202 can transmit, e.g., wirelessly, data to the IPG 200 for setting the upper and/or lower bounds within the IPG 200. The patient can operate the remote control 100 to set one or more stimulation parameters of the IPG 200. However, the IPG 200 ignores parameter settings received from the remote control 100 that are not within the upper and/or lower bounds set by the CP terminal 202. Alternatively or additionally, in an example embodiment, when the remote control 100 communicates with the IPG 200, the IPG 200 responsively notifies the remote control 100 of the restrictions set by the CP terminal 202, and the remote control 100 thereafter refrains from transmitting to the IPG 200 settings that do not comply with the restrictions, until the IPG 200 informs the remote control 100 of removal or modification of the restrictions.

Figure 3:
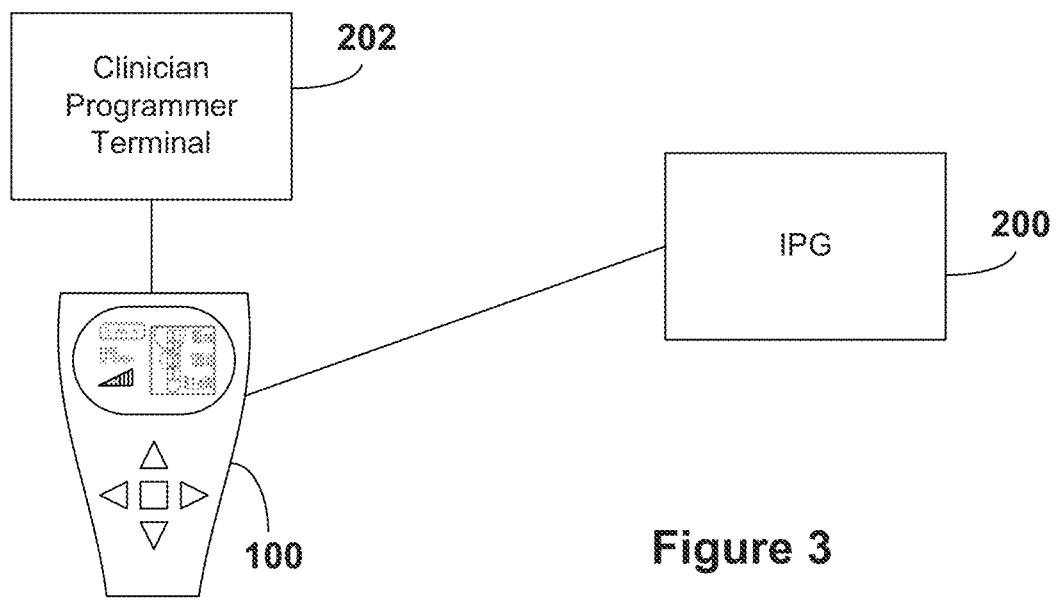
FIG. 3 shows connections between a remote control device and other system components according to another example embodiment of the present invention, aspects of the different illustrated embodiments being combinable.

In an alternative example embodiment, as shown in FIG. 3, the CP terminal 202 communicates restrictions concerning the stimulation settings to the remote control 100, and the remote control 100 refrains from transmitting instructions to the IPG 200 that do not satisfy those restrictions. For example, if the user inputs an instruction to set a stimulation amplitude to a level that is higher than an upper bound communicated by the CP terminal 202 to the remote control 100, the remote control 100 ignores the user input instruction, e.g., at least with respect to responsively transmitting an instruction to the IPG 200.

In an example embodiment, such bounds may be set in a clinical mode, such that the remote control 100 responds to a user input to modify a parameter to a level that is beyond that which is allowed by the instructions of the CP terminal 202 by accordingly modifying the GUI in the display screen 102, but refrains from sending instructions to the IPG 200 to set a parameter to the impermissible level, or, according to the embodiment described with respect to FIG. 2, the remote control 100 possibly sends the instructions, which the IPG 200 ignores according to the restrictions received from the CP terminal 202. However, as noted above, in an example embodiment, the IPG 200 can also communicate to the remote control 100 the restrictions set by the CP terminal 200. Additionally, in an example embodiment, the IPG 200 informs the remote control 100 that it is operating in clinical mode, and the remote control 100 responsively modifies its output as described above to provide the illusion of changes being implemented even though they are not being implemented.

The embodiment described with respect to FIG. 2 may be preferable over the embodiment described with respect to FIG. 3 so that if a new remote control is used, the CP terminal 202 need not resend the restrictions to the new remote control.

In an example embodiment, a clinician can put the device in a mode such that it goes on and off at various preset times, and the patient does not know when it is on or off. For example, the CP terminal 202 can send instructions concerning such a stimulation program to the IPG 200, which can, in turn, inform the remote control 100 of the stimulation program, e.g., which cannot be overridden by the patient via the remote control 100, or which can be overridden by the patient in only defined limited ways, e.g., for safety reasons. Meanwhile, the remote is configured to receive from the patient input indicating how the patient is doing. Such feedback may include input of a number on a predetermined scale. For example, the device outputs a reminder to input the information. So now clinical trial data can be obtained where information on how the patient is doing is periodically received, and the patient does not know when the device is on or off. Patient feedback may be time-stamped for subsequent clinical analysis.

Additionally, in an example embodiment, the device changes the program used to stimulate at various intervals, and the remote does not indicate to the patient which stimulation parameters are being used at that time. The patient then records over time how the patient is doing. Over time, the device learns which program is best for the patient by determining for which parameters the patient has been indicating the patient feels best. For example, the device can iterate through a number of settings for each electrode, gradually increasing the amplitude at a respective electrode contact of the leadwire, and continuously do so as long as the patient provides good feedback about that setting. In this example embodiment, the patient does have the ability to manually override the predetermined settings, for example, in case the device automatically sets a dangerous setting. Therefore, recorded feedback may include patient override requests.

In an example embodiment, there can be sensors that sense how the patient is doing. So besides for the patient manually entering how the patient is doing, the sensor information can be used to indicate how the patient is doing. Such sensors may include, for example accelerometers or other sensors that detect motor skill and/or cognitive functioning, for example, tremor (motor skill), dwell times (motor skill/cognitive), etc. The sensors may be integrated into the remote, the IPG or any other hardware that the patient carries around.

The information on how the patient is doing and the related stimulation parameters can be stored at the central server.

In an example embodiment of the present invention, the preset stimulation program, whether including a single steady set of parameter settings, or including a plurality of sets of parameter settings that are implemented at different times, e.g., at different intervals, can be set in a clinical mode, as described above, where the GUI of the remote control 100 is modified to reflect changes entered by the patient, although such changes are not implemented. In an example embodiment, even in a clinical mode, the system may allow the user to override certain settings for safety reasons.

According to an example embodiment of the present invention, the system may be configured to perform a clinical study for testing various settings, including, for example, testing a response to an on-low setting at which a low power stimulation is applied, an on-high setting at which a high power stimulation is applied, and an off setting at which no stimulation is applied. In an example embodiment the clinical stimulation program includes cycling through the three (or more) settings one or more times at equal or varying intervals. As explained above, the patient can be blind to the changes, and the system can be configured to record information regarding the patient's condition at various points during the stimulation program, which information can be obtained from user input and/or from sensors.

In an example embodiment of the present invention, the system may include an electronic diary ("e-diary") feature for recording a log of time-stamped patient condition information, and for recording time-stamped information concerning the stimulation settings, so that the patient condition information can be associated with particular stimulation settings. Certain of the recorded information can pertain to factors that are not a result of the stimulation settings, e.g., which medication(s), if any, the patient is taking. Other of the patient condition information can be associated with a combination of the stimulation settings and the medication(s) the patient was taking at the time associated with the patient condition information.

In an example embodiment of the present invention, for obtaining patient condition information, medication information, etc., the remote control 100 includes user input hardware and/or software controls via which the patient can enter information. In an example embodiment, the remote control is configured to receive input from the patient of entry of a number on some number scale, e.g., 1-10, of how the patient is feeling. In an example embodiment of the present invention, the remote control 100 includes a "good" button and/or a "bad" button by which the patient can generally indicate whether the patient generally feels good and/or bad. In an example embodiment of the present invention, the remote 100 includes soft and/or hard buttons (or check boxes, radio buttons, etc.) for predetermined significant events, such as, for example, falls, seizures, etc., which the patient can select when such an event occurs. The system can record a time-stamped entry in the e-diary noting the occurrence of the event indicated by the selection of the corresponding event input.

In an example embodiment, the remote control 100 stores the e-diary information locally in a long-term storage of a memory device of the remote control 100. In an example embodiment, the remote control 100 alternatively or additionally transmits the e-diary information to the IPG for storage therein. In an example embodiment of the present invention, the e-diary information is alternatively or additionally uploaded to a central server, e.g., as discussed above under the "Cloud Data Management" section.

As noted above, in an example embodiment the system is configured to record a time-stamped log of the stimulation settings. In an example embodiment, the IPG records time-stamped stimulation settings at predetermined intervals. In an alternative example embodiment, the IPG records time-stamped stimulation settings responsive to a change to the stimulation settings. In an example embodiment, after recording initial settings, subsequent settings are recorded as a change to the immediately preceding settings.

In an example embodiment of the present invention, the system correlates respective portions of the patient-condition information to respective settings based on the time-stamps, and automatically modifies settings based on the correlation. For example, in an example embodiment, the system detects a trend, e.g., that with increase of a certain parameter between a first time and second time, the patient condition has deteriorated, and therefore modifies the settings, e.g., in a reverse direction in response to a detected deteriorated condition and/or further in a same direction in response to a detection improvement in condition.

In an alternative example embodiment, or additionally, the system outputs a report of the effects of the settings on the patient condition. For example, in an example embodiment, the system outputs a report that an increase or decrease of parameter 'x' has been detected to be associated with a deterioration or improvement of condition 'y'.

In an alternative example embodiment, or additionally, the system outputs a timeline covering a time period including some or all of the time-stamped times and further outputs against the timeline (a) a graph representing changes to one or more patient conditions indicated by the patient-condition information, and (b) identifications of the settings prevailing at different times of the timeline.

VOA Selection for Target Volume

A target volume can be selected, e.g., by a user or by the system, e.g., based on clinician input, the patient's information (such as a patient disorder, patient history, etc.) population information (such as learned information from one or more other patients), therapeutic goal, etc. In an example embodiment of the present invention, the system outputs suggested stimulation settings and/or outputs a graphical VOA corresponding to suggested stimulation settings for such a target volume.

Figure 4:
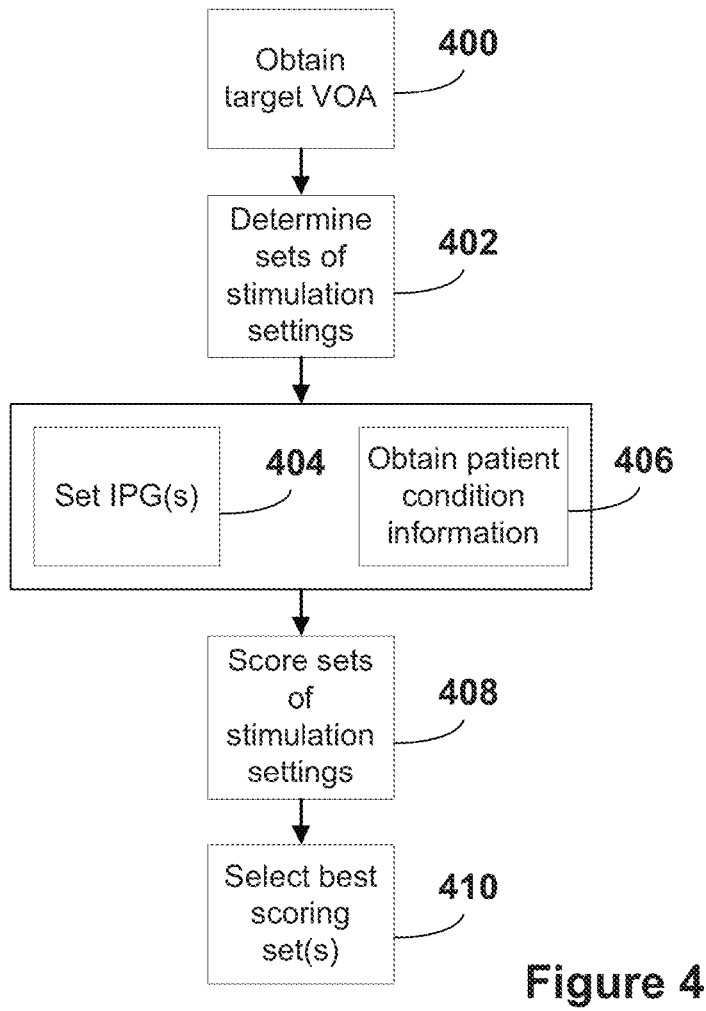
FIG. 4 is a flowchart that illustrates a computer-implemented method of refining target volume selection, e.g., over time, according to an example embodiment of the present invention.

Referring to FIG. 4, at step 400 the system obtains a target volume. At step 402, the system determines a plurality of sets of stimulation settings that provide VOAs considered similar to the target volume. The system can perform such a determination according to a predetermined one or more conditions, such as a degree to which a VOA must overlap the target volume and/or a maximum amount by which the VOA can spill beyond the boundaries of the target volume. At step 404, the system sets the IPG of one or more patients, e.g., for whom the target volume (or a similar target volume) is obtained, to test each of the plurality of sets of stimulation settings. The settings may be tested on a single patient, e.g., the particular patient for whom the system will output the suggested optimal settings in view of the obtained target volume, or across a patient population. According to an example embodiment, where the settings are tested across a patient population, different ones of the sets of stimulation settings can be tested in parallel. According to an example embodiment, where the settings are tested by applying the sets of stimulation settings to a single patient, the system cycles through a program in which different sets of the stimulation settings are applied in a sequence over time, different ones of the sets being applied during different intervals of the program.

At step 406, the system obtains patient condition information for the tested settings. Steps 404 and 406 may be performed concurrently. That is, while a patient is stimulated by a set of stimulation settings, the system is configured to obtain information concerning the patient's condition, e.g., via patient input or by sensor signals, as described above. The information and settings can be time-stamped.

In an example embodiment, for each of the patients on which the sets of stimulation settings are tested, the system associates the patient condition information with the set of stimulation settings applied to the respective patient for whom the respective patient condition information was obtained, the association being based on a determined correspondence of the timestamps of the patient condition information and the applied set of stimulation settings, as explained above.

In an example embodiment, at step 408, the system assigns a score to each of the sets of stimulation settings based on the patient condition information associated with the respective set. For example, different weights can be applied to different types of patient condition information to calculate an overall score. According to an embodiment in which the sets of stimulation settings are tested across a patient population, the system can test a same one of the sets on multiple patients. In an example embodiment, the system calculates an average score of the scores calculated for each patient for whom the set of stimulation setting was applied.

At step 410, the system may compare the calculated scores and select a predetermined number or percentage of the best scoring, e.g., the 3 highest scoring or the single highest scoring, tested set(s) of parameter settings as candidate parameter settings (and associated VOAs) to output as suggestions for a patient for whom the same or similar target volume is selected.

The target volume selection and/or the selection of suggested settings can be performed on any computing device, e.g., a CP terminal.

In an example embodiment of the present invention, the sets of settings can be tested in a clinical mode during which the patient is blinded to the settings.

Programming Based on IPG Efficiency

It is possible for a plurality of different sets of stimulation settings to result in the same or similar VOAs, where certain ones of the sets of stimulation settings are more electrically efficient than others of the sets. For example, similar tissue activations may be obtained by varying the electrical amplitude and pulse width. For example, first settings have a high amplitude and a short pulse width can be equivalent or approximately equivalent to second settings having a lower amplitude but a longer pulse width.

In an example embodiment of the present invention, the system can in step 402 select a plurality of electrically equivalent settings that in their respective amplitudes and pulse widths. It is noted that although such sets of settings may be considered electrically equivalent and/or calculated to produce equivalent or substantially equivalent VOAs, it may nevertheless occur that the different sets of settings produce different clinical effects. Therefore, in an example embodiment, the system tests these equivalent sets at steps 404 et seq.

In an example embodiment of the present invention, the system also assigns a weight to electrical efficiency for the calculation of the scores at step 408.

In an example embodiment of the present invention, the system finds a plurality of sets of electrically equivalent stimulation settings using a strength/duration curve. For example, in an example embodiment, at step 402, the system determines a set of stimulation settings that is estimated to produce a VOA that best fits the target volume, and then finds other sets of stimulation settings that are electrically equivalent to the determined set of settings based on the strength/duration curve.

According to an example embodiment of the present invention, the system uses a strength/duration curve that relates to how the discharge of an IPG. In an example embodiment, a device is programmed, e.g., automatically, to use the least amount of energy to fill the target volumes based on the strength/duration curve. In an example embodiment, the efficiency of the settings is one of a plurality of factors contributing to a score on whose basis a set of settings is selected, as described above, where, all else being equal, greater efficiency results in a higher score.

In this regard, according to an example embodiment, programming settings are automatically adjusted towards a target volume specified by a user (or otherwise selected). The visualization system is configured to, based on the specified target volume, test settings that use the lowest power consumption while reaching the specified target volume. In an example embodiment, the system also tests settings that yield volumes that approximate the target volume (e.g., slightly larger or smaller than the target volume). Additionally, in an example embodiment, the testing of such settings can be performed during the clinical mode, so that the optimal settings (in terms of a combination of therapeutic effectiveness and power consumption) is obtainable with the aid of feedback from a blinded user.

Figure 5:
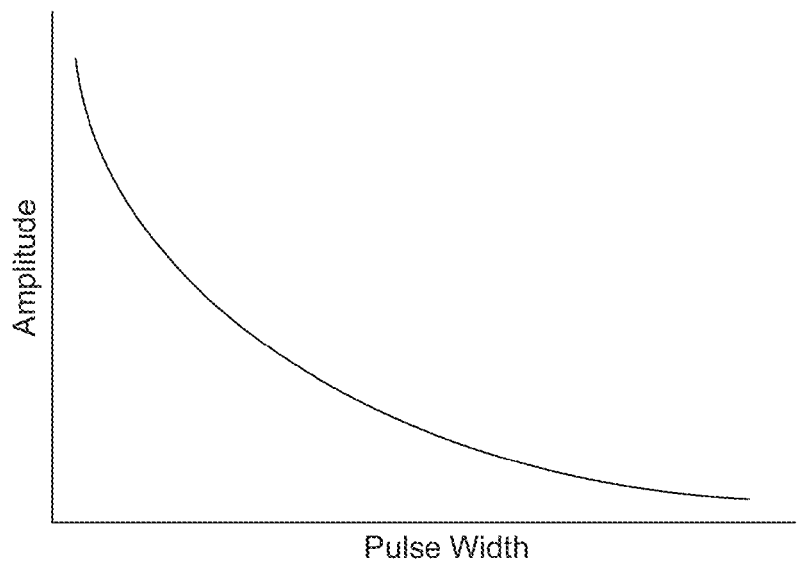
FIG. 5 is an example strength/duration curve plotting different combinations of power and pulse width values estimated to provide equivalent stimulation, according to an example embodiment of the present invention.

FIG. 5 shows an example strength/duration curve, where the ordinate represents the amplitude and the abscissa represents the pulse width, where the plotted points are all estimated to produce substantially equivalent volumes of activation. The graph shows that the higher the amplitude, the shorter the required pulse width for producing substantially the same volume of activation. That is, a fiber is expected to fire based on a combination of amplitude and duration of the stimulation at that amplitude, so that the higher the amplitude, the shorter the required duration for causing the fiber to fire.

According to an example embodiment of the present invention, for a selected VOA, the system plots the strength/duration curve of values that are estimated to produce the selected VOA, and selects the most efficient of the pairs of values, e.g., assuming all other factors being equal (as noted above, other factors may result in selection of a set of values different than those of the most efficient pair).

For example, the system can obtain a target volume, e.g., user-selected or automatically selected. The system then determines one or more closely matching producible VOAs. The system is configured to select, for each of one or more of such VOAs, a most energy efficient pair of amplitude and pulse width values to produce the respective VOA. For example, where a remaining battery power is 3.7v and a required amplitude is more than 3.6 volts, the system can use capacitors to double the voltage to 7.4v. If less than 7.4v is required, the system can burn off the difference between 7.4v and the required voltage. For example, if 4v is required, the system can burn off 3.4v, which is inefficient. Accordingly, for the 4v requirement, the system can determine from the strength/duration curve whether there is a more efficient pair of settings. For example, the system might determine that the same VOA is producible with a longer pulse width at 3.5v.

SFM Analytics

Example embodiments of the present invention pertain to determining a target volume by analysis of VOAs for a plurality of patients.

According to an example embodiment of the present invention, a system can include program code for providing visualization features to output graphical representations of estimated VOAs, e.g., about a representation or image of an implanted leadwire and/or overlaying a model or image of a patient anatomy. The system can include code by which user, e.g., clinicians or patients, can test various settings estimated to produce such VOAs. The system can also include analytics code for determining a target volume, e.g., based on such VOAs tested by the users.

In an example embodiment of the present invention, the system includes features for facilitating the sharing by users of target volumes the different users have selected. In an example embodiment, the system includes features by which user can share data, such shared data being subjected by the system to analytics to determine optimal target volumes and/ or optimal stimulation settings and corresponding VOAs.

Systems Configurations:

In an example embodiment of the present invention, the SFM analytics features are provided as part of a stand alone visualization system. For example, A Guide system can be used to modify/test parameter settings corresponding to VOAs and/or side effect volumes (volumes where stimulation is preferably avoided), and/or to set target volumes, which VOAs, side effect volumes, and/or target volumes can be transported to a separate analytics system on which analyses can be run. In an alternative example embodiment of the present invention, the SFM analytics features are provided in a Guide system including the clinician programmer features by which to program the settings of the IPG, such that the analytics by which to find optimal settings is conveniently on a system used to actually program the implanted device.

According to an example embodiment of the present invention, analytics information and input for performing analytics can be stored remotely via a cloud/internet-based system. In an example embodiment, the data from many systems, e.g., workstations operated by many users, can be stored centrally, and the centrally stored data and/or the resulting analytics information can be accessed by a plurality of users of networked systems.

In an example embodiment, the analytics features are provided in a software package that users can load onto the users' computers. Alternatively, the analytics features can be provided as a web-based application.

In an example embodiment of the present invention, the system is configured to allow a user to limit access to the data associated with the user, e.g., data created by the user or about the user, to only certain users (e.g., only one or more certain specified users or only users of one or more certain specified user groups) or to only certain systems (e.g., only via the Guide system). For example, the system can require entry of a user ID by which the system determines whether a user is authorized to access such restricted data.

It is noted that the analytics software and the input and/or output data can be at different locations.

Analyses of the SFM Analytics:

1. Population Overlap:

According to an example embodiment of the present invention, the SFM analytics system obtains as input a group of VOAs from a population of patients, where each VOA is associated with a measure of effectiveness, and the SFM analytics system determines a target volume based on the input information. For example, a collection of VOAs can form a group to be subjected to the analytics calculations where there is a clinically significant commonality between the VOAs of the collection. For example, VOAs of patients who share a certain diagnosis, e.g., the patients all have Alzheimer's disease, can form a clinically significant group for analysis to determine a target volume for treating Alzheimer's disease. Another or alternative significant commonality can be that the VOAs are associated with similar anatomical locations at which the stimulation electrode is implanted.

According to an example embodiment, the system is configured for a user, e.g., a physician, to manually create a group of VOAs to be used as input to analytics functions. For example, a physician might notice that a number of VOAs of stimulation settings applied to one or more patients provided excellent results, and the user can form a group for such VOAs. A single VOA can be a part of multiple groups.

In an example embodiment, for the analysis of a group of VOAs, the system places all of the VOAs in a common spatial reference space. For example, the system is configured to transform one or more, e.g., all, of the VOAs into a common atlas space. This may be required for example where the VOAs were obtained for different patients whose anatomical makeup varies.

The system is configured to determine where the VOAs of the common reference space spatially overlap for determining a target volume. For example, the system can output a combination of a collection of points, e.g., voxels, that belong to all or a threshold number or percentage of the VOAs of the group as a target volume. In this regard, VOAs each encompass a collection of points, e.g., voxels.

Alternatively, the system can perform more complex calculations for finding voxels of significance shared by some of the group of VOAs, the combination of voxels of interest forming a target volume.

For example, in an example embodiment, the system is configured for obtaining ratings for each of the group of VOAs, e.g., one or more ratings for some characteristic, e.g., how well it helped the patient with respect to some score. For example, clinicians can input into the system a rating on how well the patient is doing against some standardized scale.

The system is configured to assign a greater weight to those VOAs associated with better scores, e.g., the greater the score, the greater the weight. For example, the system can weight each point, e.g., voxel, within a VOA by the VOA's score. Then the system calculates for each of the points within any one of the group of VOAs, a respective score based on the combined weighted scores of the point across all VOAs of the group that include the respective point. For example, the system can sum the scores for each of the points. Alternatively, the system can average the scores for each of the points. According to the latter embodiment, the system also takes into consideration the number of VOAs in which the point is included. For example, a score of 0, a negative score, or some other value can be assigned to a point for a VOA in which it does not appear. Alternatively, the number of VOAs of the group in which the point is included can be considered as a separate factor in the calculation. According to an example embodiment of the present invention, the system compares each point's value to a threshold, and includes a point as part of an output target volume if the point's score meets the threshold. According to an example embodiment of the present invention, the system selects a threshold number or percentage of highest scoring points as the target volume.

According to an alternative example embodiment of the present invention, the above described thresholding can be performed to produce a volume which the system can subject to further calculations from which to select a target volume for output.

2. Group Comparisons:

In an example embodiment of the present invention, the system is configured to compare different groups of VOAs to determine target volumes of stimulation and/or volumes to be avoided, e.g., so as not to produce an unwanted side-effect.

For example, a first collection of VOAs associated with a certain side effect can form a first VOA group and a second collection of VOAs not associated with the side effect can form a second group. The system can automatically create these groups. Alternatively, a user can manually form the groups and input an instruction to the processor to perform a comparison.

The system is configured to transform the VOAs to a single common atlas space and find an area included in the group associated with the side effect and not included in the group that is not associated with the side effect, and output the area, e.g., in relation to an atlas space, as an area that should not be stimulated.

Alternatively, a more complex calculation can be used to determine the points of the area to be avoided. For example, each point can be individually scored based on a combination of scores of all VOAs of the group associated with the side effect and in which the respective point is included, e.g., where the score for a point within a VOA depends on the severity of the side effect for that VOA. In an example variant of this embodiment, the system first finds which areas are included in a threshold number and/or threshold percentage (e.g., 100%) of the VOAs associated with the side effect and not included in a threshold number and/or percentage (e.g., 100%) of the VOAs not associated with the side effect. For voxels in the identified area, the system assigns respective scores based on the severity of the side effect for the VOAs in which the voxel is included. Alternatively, for each voxel, the system assigns a score based on a combination of those VOAs associated with the side effect an in which the voxel is included and of those VOAs not associated with the side effect. For example, inclusion in a VOA associated with the side effect can contribute to a higher side effect score, the extent by which the score is raised being dependent on the quantified severity of the side effect with which the VOA is associated; and inclusion in a VOA not associated with the side effect can contribute to a lowering of the score of the voxel. The system includes those points whose combined score meets a predetermined threshold, or a threshold number or percentage of points sorted by score, as the volume to be avoided.

Similarly, in an example embodiment of the present invention, where a benefit is associated with a first group of VOAs and is not associated with a second group of VOAs, the system finds the points, e.g., voxels, that are included in the VOAs of the group associated with the benefit and not included in the group that is not associated with the benefit, or scores points by the extent of their inclusion in one group over the other group, as described above, to output the combination of such points as a target volume.

3. Analysis of VOA Overlap with Target Volume:

According to an example embodiment of the present invention, the system is configured to quantify the extent to which a VOA meets a target volume based on a spatial difference of the VOA and the target volume. For example, the extent to which the VOA extends beyond the target volume, the extent to which the target volume extends beyond the VOA, and the extent to which the VOA and the target volume overlap contribute to an overall score of the VOA. See, for example, U.S. Provisional Patent Application Ser. Nos. 61/521,572, filed Aug. 9, 2011 and 61/549,053, filed Oct. 19, 2011, the entire content of each of which is hereby incorporated by reference herein.

According to an example embodiment of the present invention, the system is configured to determine how well a group of VOAs meets a target volume. For example, the system determines a spatial difference between the group of VOAs and the target volume. For example, the system assigns to each VOA of the group a score indicating how well the respective VOA meets the target, and a combination of the scores can be used as a metric to determine how well the group meets the target volume. For example, a particular set of parameter settings might be common to all of the VOAs of the group, and it may be useful to know the extent to which the settings are expected to produce a VOA that substantially meets the target volume. The score can be used as a metric of the expectation.

Alternatively or additionally, the determination of the extent to which the group of VOAs corresponds to the target volume can be performed for the VOAs as a whole, by which the system calculates a mean and/or standard deviation to rate the VOAs as a group.

According to an example embodiment, the system outputs a number indicating how many or the percentage of the VOAs of the group that meet a certain threshold correspondence with the target volume.

According to an alternative example embodiment, for each point that is included in any of the VOAs of the group, the system determines the number of the VOAs of the group in which the point is included and includes the point in a composite volume if the point is determined to be included in a threshold number or percentage of the VOAs of the group. The system compares the composite volume to the target volume and scores the composite volume based on the degree of similarity between the target and composite volumes. The system outputs the score as a rating of the correspondence between the group of VOAs and the target volume.

According to an example embodiment of the present invention, a similarity of an average center of mass of the group of VOAs and the center of mass of the target volume is a factor used by the system to calculate the rating of the correspondence of the group of VOAs to the target volume.

4. Other Analyses:

SFM analyses can include analysis of variance (ANOVA), generalized linear models, parametric or non-parametric techniques, Bayesian analysis, etc.

Obtaining Analysis Paradigms and/or Data for Analysis

According to an example embodiment of the present invention, the system includes features by which to collect VOA related data over time to then be subject to an analysis, for example, one or more of the analyses described above. According to an example embodiment, the system is configured such that, where a user begins compilation of a parameter set of an analysis to be conducted on an input set of data, e.g., an input set of VOAs, as described above, the user is able to save the constructed analysis paradigm and retrieve it a later time, e.g., for modification and/or application to a set of data input. In an example embodiment, a saved analysis paradigm may function as a template, e.g., which can be copied as a new analysis paradigm, which copy can be further modified. Moreover, the data collection to which an analysis is applied can be a parameter of a saved analysis paradigm. A template can be copied multiple times, and modified to be applied to different sets of data.

In an example embodiment, an analysis template can be saved without specification of a data collection to which the analysis is to be applied. Such a template can be copied as a new analysis record and modified to specify the data collection on which the analysis is performed and to include results of such an analysis. Multiple copies can be saved, each specifying, for example, a different data collection.

For example, an analysis paradigm can be set up by which to find spatial differences between two different types of groups, Group A data set and Group B data set. Further, the analysis can be set with, for example, certain thresholds to rate the data (e.g., threshold overlap or threshold difference), certain statistical tests to be applied, etc. Thus, there can be a number of parameters to use for an analysis. Such a paradigm specifying one or more of such variable parameters can be saved as a template, and copied as new analysis paradigms to which to apply different data sets or modified analysis parameters, for which a user can select an activation instruction, in response to which the system runs the modified analysis on the respectively specified data. For example, the system may display a "run" button in a GUI, in response to selection of which, the system runs the specified analysis.

According to an example embodiment, the templates can be stored as a data structure that can be shared by users. For example, in an example embodiment, a template can be attached to an e-mail which a one user can send to another user, which other user can open and modify or otherwise use the attached template, e.g., where the other user also includes the software adapted to interpret the data structure. Alternatively or additionally, the template can be stored in a central location accessible by a plurality of terminals on which the software is run. In an example embodiment, the data collection, e.g. VOAs and/or associated stimulation parameters, to which the analysis is applied can also be shared e.g., separate from the template and/or as part of the template.

According to an example embodiment of the present invention, the system is configured for storing associated groups of data, e.g., groups of VOAs and/or associated stimulation parameter sets, which groups can be opened by a user to be subjected to various analyses. The groups can further be modified over time. For example, in an example embodiment, the system includes an interface, e.g., a graphical user interface and/or other interface, via which to receive user input for specifying a set of stimulation parameters and/or associated VOAs, and/or via which to output the set of stimulation parameters and/or graphical representations of such VOAs. The system further includes, according to an example embodiment, a selectable menu item, such as an option of a "File" menu selectable from a toolbar, which, when selected allows the user to save the presently open stimulation settings and/or VOA to a database folder representing the group. If no folder representing the group has been previously set up, or if the user otherwise wants a new group, the system allows the user to select "New Folder" or "New Group" or the like to create the folder/group with which to associate the open settings and/or VOA.

In an example embodiment of the present invention, the system displays in a GUI selectable graphical representations of groups that have been previously created, provided for user selection to associate a set of stimulation parameters and/or a VOA that is in focus with the selected group representation. In an example embodiment, the set of settings and/or VOA can be added by drag-and-drop. For example, an icon representing the set of settings and/or VOA that is in focus, e.g., that is displayed, is selectable and can be dropped onto one of the group representations to be included as part of the group. Each stored group can be separately subjected to one or more analyses. In an example embodiment, the system also includes an icon for creating a new group, which is selectable and/or to which a set of stimulation settings and/or a VOA can be dropped, in response to which selection or drop, the system provides for a user interaction by which to name a new group to which the set of settings and/or VOA that is in focus can be added.

For example, as a clinician notices various symptoms associated with a particular VOA, the clinician can use the GUI features to drop the VOA into various "buckets" that can later be used for analysis. For example, the clinician notices eye movement, and therefore associates the VOA in focus with a bucket of VOAs that resulted in eye movement. In this regard, a VOA and/or a set of stimulation settings can be associated with more than one data group, and can be subjected to analyses of such different groups and/or subject to different types of analyses. At any point in time, a user can use the system to subject such a bucket to an analysis, during which the system performs an analysis, e.g., as described herein, on those volumes that are included in the bucket. It is noted that the system can similarly maintain buckets of side effect volumes and target volumes on which analyses can be run.

Various kinds of data can be associated with VOAs (or other volumes), by which the VOAs (or other volumes) can be filtered. Such data can include, for example, diagnosis, age, gender, medication used, clinical test scores, patient assessment of well being, target volume with which the VOA and/or stimulation settings are associated, variance of a medical image of a patient with which the VOA and/or stimulation settings are associated from a standard atlas, quantitative data from a measurement device such as an accelerometer, of a sensor whose signals can have a certain significance, e.g., indicating tremor, straightness of lines, dwell time, etc. According to an example embodiment, a user can filter stored VOAs (or other volume types) and/or sets of stimulation settings by such data, and apply the filtered group to an analysis. For example, with respect to variance between medical image and standard atlas, a user might want to filter out those VOAs and/or settings that are associated with a patient whose medical image(s) varies from a standard atlas by a threshold amount, since results of a stimulation applied to such a patient may be expected to be different than those normally expected from a patient whose anatomy more closely corresponds to the typical anatomical arrangement. Aside from entering filter parameters for obtaining a matching set of volumes to be immediately subjected to an analysis, the system is also configured to provide for filtering of the volumes to obtain a filtered set that can be stored as a new bucket, which can later be retrieved, e.g., for running one or more analyses.

Creation and Sharing of Target Volumes

According to an example embodiment of the present invention, a system is provided that provides for a cycle of testing stimulation settings that produce corresponding VOAs, obtaining results of such tested settings, analyzing such results, selecting a refined target volume based on such analyses, and selecting new stimulation settings to be tested. A refined volume can be selected, e.g., by changing the volume's position, orientation, size, shape, etc. Moreover, in an example embodiment, such modifications can be performed graphically, e.g., by manipulation of graphically displayed nodes.

This cycle can be repeated, e.g., continuously, to refine the stimulation settings. Moreover, the testing can be of stimulation settings of a plurality of patients and the analyses can be of results of such tested settings and/or their corresponding VOAs of a plurality of patients.

Figure 6:
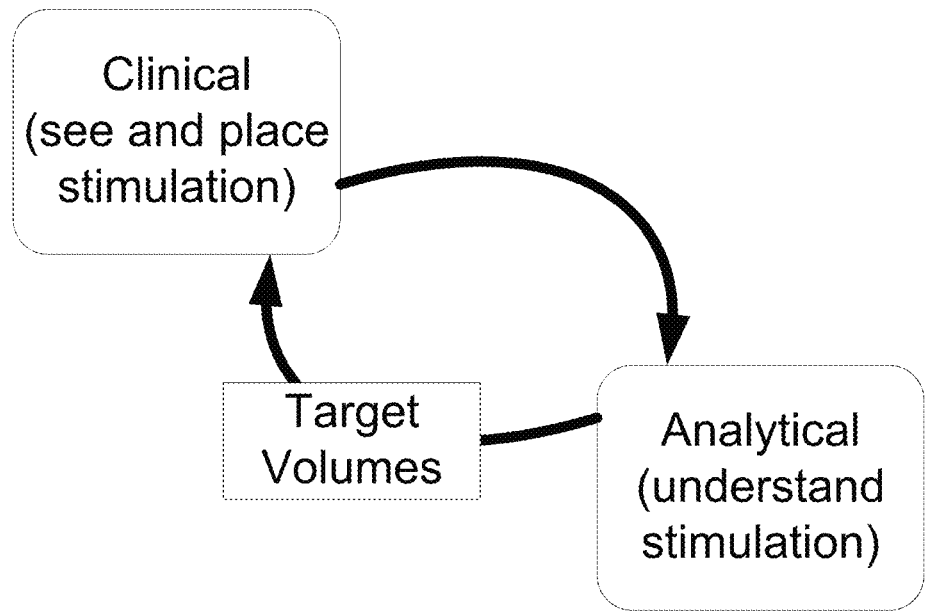
FIG. 6 is a diagram that illustrates a stimulation and analysis cycle by which target volumes and/or stimulation settings can be refined, according to an example embodiment of the present invention.

For example, information concerning such settings, their corresponding VOAs, and respective results of stimulations using such settings can be stored at a single location for access by one or more clinicians who can set new target volumes and/or choose modified target stimulation regions based on results of the analyses. FIG. 6 illustrates the stimulation and analysis cycle by which target volumes and/or stimulation settings can be refined.

Figure 7:
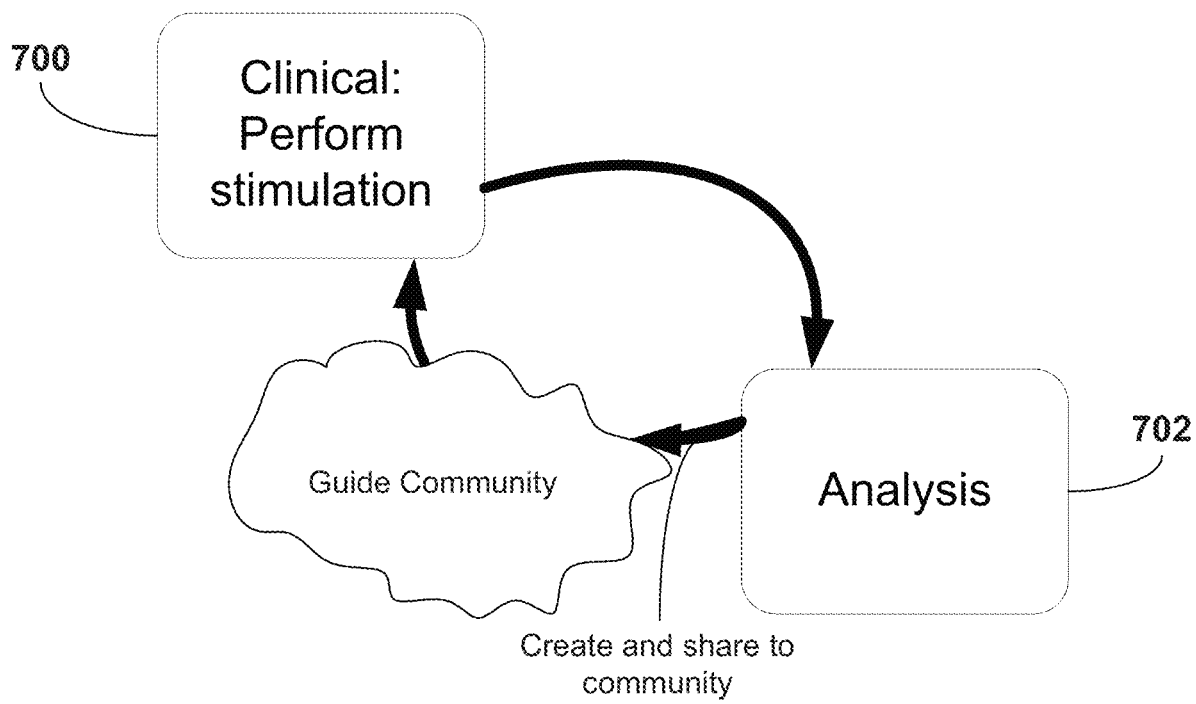
FIG. 7 is a diagram that illustrates a stimulation and analysis cycle with volume sharing, according to an example embodiment of the present invention.

FIG. 7 shows a modified cycle according to an example embodiment of the present invention, according to which users are able to share and/or publish their discovered and/or input target volumes for implementation by other users. For example, at a step 700, a guide module can transmit stimulation settings to an IPG for application of those settings to electrodes of an implanted leadwire to stimulate an anatomical region of a patient. At step 702 an analysis can be performed on the tested settings, corresponding VOAs, and/or results of such stimulations, tested by one or more clinicians on one or more patients. At step 704, a user can select a new target region based on the analysis, and share it with a community of users, e.g., clinicians, researchers, and/or other users, who can use such a shared target region to select new stimulation settings to test at 700.

Figure 8:
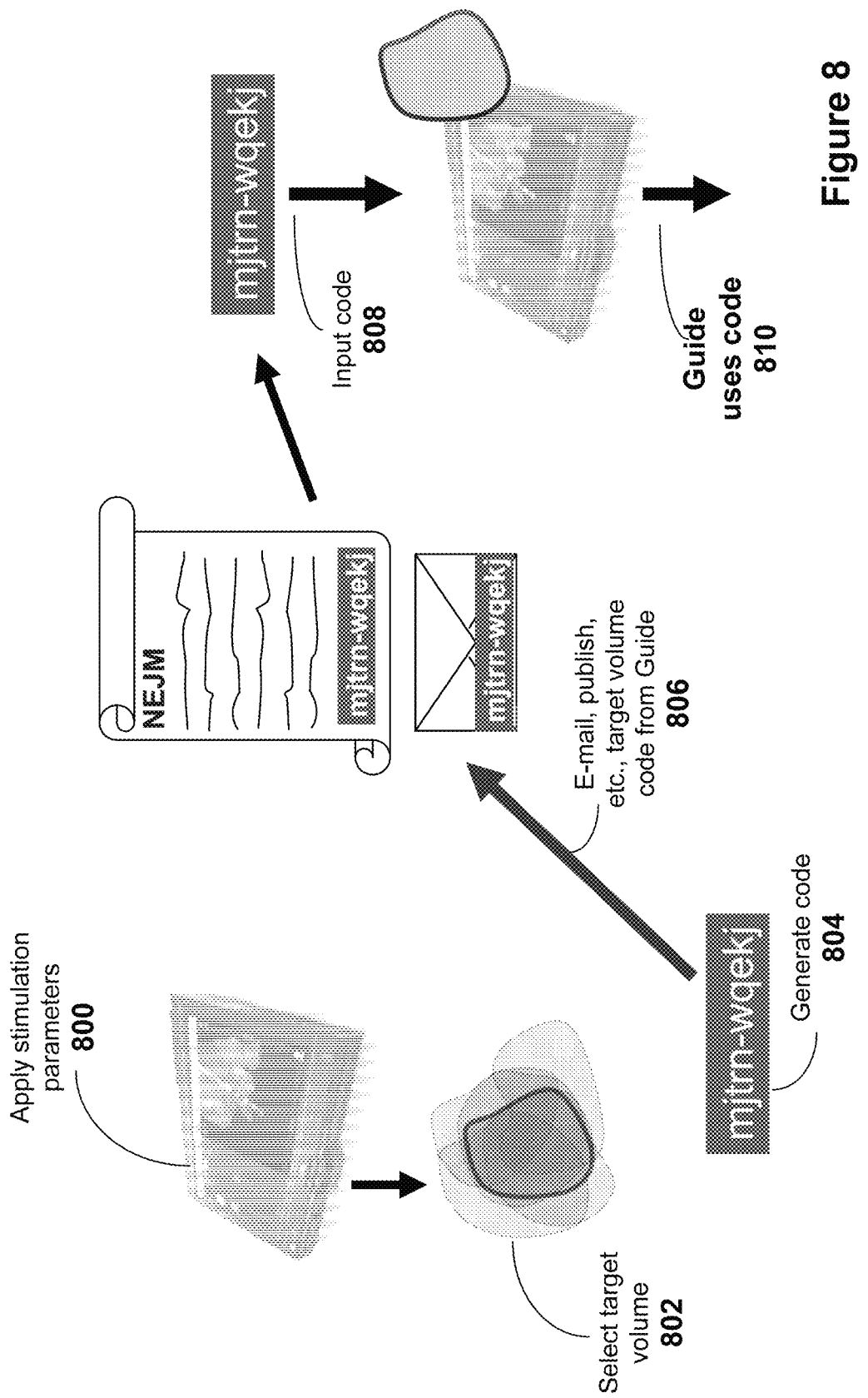
FIG. 8 illustrates a data flow including volume sharing, according to an example embodiment of the present invention.

Referring to FIG. 8, according to an example embodiment, at step 800, a first doctor, "Dr. A," uses a Guide module on a workstation, to set stimulation parameters, view a corresponding VOA, apply the settings to an IPG and an implanted electrode leadwire, and/or record results of such stimulation settings.

At step 802, Dr. A selects a target volume based on the results of the applied stimulation settings. (It is noted that a different doctor may instead select the volume. It is also noted that the newly selected volume can be based on analysis of results of settings applied to more than one patient by more than one doctor. It is also noted that the selection of the new target volume can be further based on results of a plurality of different applied sets of stimulation settings. It is also noted that the analysis can be manual or can be automatic, e.g., using one or more of the analyses described above.)

At step 804, the Guide module generates a code for the target volume set by Dr. A. For example, Dr. A selects an option to save the input target volume and the system responsively generates and outputs a code associated with the saved target volume. For example, Dr. A can save the target volume under any descriptive name by which Dr. A can later identify the target volume in a useful manner, but the system can store a field, that includes the generated code, in association with the saved target volume. Further, in an example embodiment, the field can be opened for view by Dr. A so that Dr. A can later identify the code if otherwise forgotten. For example, in an example embodiment, responsive to right-clicking a representation of a file corresponding to the target volume, the user is able to view properties of the file, including the generated code. Alternatively, when the target volume is opened by Dr. A, the system also displays the code. (In an alternative example embodiment, the doctor manually enters a code, and the system is configured to inform the doctor whether the entered code is available.)

At step 806, Dr. A shares the code with one or more other doctors. For example, Dr. A e-mails the code or otherwise publishes the code. At step 808, Dr. B inputs the code into an instantiated Guide module running on Dr. B's terminal, in response to which the Guide module into which Dr. B input the code displays or otherwise uses the target volume selected by Dr. A and for which the code was previously generated. For example, in an example embodiment target volumes are accessible via an alphanumeric code that is published so that other users can then use the code to access a central server that provides them with the target volume, e.g., they can be downloaded via a webpage of the cloud.

In an example embodiment, when other users import such published volumes, the system provides for the importing user to tag the imported volume, for example, with data identifying who generated the volume, in which facility the data was generated, etc., and to store the tagged volume in a folder owned by the importing user. In an alternative embodiment, the system is configured to automatically append such metadata, e.g., which can be accessed by the importing user.

The target volume selected at step 802 can be generated manually by Dr. A, e.g., by manipulation of graphical nodes in a user interface, or can be generated automatically by the system based on input, e.g., selected by Dr. A. For example, Dr. A can input a group including a plurality of sets of stimulations settings, corresponding VOAs, and results into a system-run analysis, e.g., one of the analyses described above, based on target generation parameters (pre-programmed and/or user input) of which the system outputs the target volume, which Dr. A can select for saving.

Dr. A can store a plurality of target volumes. For example, different ones of the stored target volumes can be associated with different groups of patients. For example, different target volumes can be associated with different desired therapeutic effects, different diseases, different indications, etc. In an example embodiment, the system enables the user to identify the characteristic with which the target volume is to be associated. For example, a file name or folder name can be used to identify the characteristic.

While the above discussion concerning sharing of volumes, e.g., in connection with FIG. 8, has been described with respect to target volumes, in an example embodiment, the system also provides for a user to likewise share side effect volumes. For example, Dr. A can manually enter a side effect region where stimulation is to be avoided or the system can automatically generate a side effect region, e.g., as described above in the "Group Comparisons" section. The system can assign a code to the side effect region, which code can be shared as described above with respect to the target volumes.

In an example embodiment of the present invention, the system stores the user-defined/selected target and/or side effect regions at a central location accessible by a plurality of terminals running a Guide module. It is noted that a number of users can also use a single terminal using different log-in information. The different users of the same or different terminals can thereby obtain, from the central location and via a network, e.g., the Internet, the stored target and/or side effect region previously selected by a different user. The user can identify which volume to obtain by entering the corresponding code.

In an alternative example embodiment, the system generates a code for the selected target or side effect volume based on characteristics of the volume. In an example embodiment, the generation of the code based on the characteristics of the volume is such that the system is able to reconstruct the volume based on the code. For example, the code may be based on one or more of a center of mass of the volume and spatial coordinates of a perimeter of the volume. Other characteristics of the volume as described above with respect to data stored to represent a volume can additionally or alternatively be used. Accordingly, the volume need not be stored. Instead, a user can share a selected volume by sharing the code generated by the system, and another user can enter the shared code, in response to which the system outputs the volume reconstructed based on the code.

In an example embodiment, when a first user, using the Guide software to program a patient, enters a code to open a volume shared by a second user, the system is configured to modify the shared volume to reflect an anatomy of the patient. For example, the shared volume might have been generated in a space corresponding to the brain of a different patient or in a generic atlas space, which varies from the anatomical space corresponding to the brain of the currently active patient information.

In an alternative example embodiment the system initially opens the volume according to the spatial environment in which it is saved or according to a generic atlas space (even if the volume was generated in relation to an anatomical space of another patient), and subsequently, in response to a user conversion instruction, transforms the volume to reflect the anatomy of a currently active patient. According to the embodiment in which the code is automatically generated based on characteristics of the volume, in an example embodiment the system is configured to, when a user selects to open the shared volume, open the volume in a generic atlas space, and the user can instruct the system to convert the volume to the patient anatomical space.

The volume being shared can be stored by the system in a manner by which it is not associated with any patient for whom the shared volume was created, in order to preserve the patient's privacy. For example, as noted above, even if the volume is generated in relation to an anatomical space of a patient, the system can be configured to output the shared volume transformed to a generic atlas space. Alternatively, the patient-specific anatomical space can be output since it cannot be used to easily identify the patient.

The system thus facilitates a continuous cycle of refinement of volumes. For example, a first clinician can open a number of target volumes selected by one or more other clinicians based, for example, on similar findings reported by the one or more other clinicians. The user can then have the system run an analysis to find overlapping regions of the multiple target volumes, as discussed above, to thereby form a further refined target volume.

In an example embodiment of the present invention, the system further includes an option to automatically generate a target volume based on a combination of VOAs that correspond to the multiple selected target volumes. For example, in response to receipt of user input selecting the option to generate the target volume based on the underlying VOAs, the system is configured to find for each of the selected target volumes a best fit set of stimulation variables to provide a respective best fit VOA. The best fit parameter settings and VOA can be patient-specific to a currently active or selected patient. The system then performs the analysis upon the plurality of VOAs to find a new target volume (for which the system is configured to also find a further set of best fit parameter settings and corresponding VOA).

Alternatively, the user can have the system graphically overlap the multiple selected target volumes of the one or more other clinicians or the corresponding best VOAs, and manually outline a new target volume based on the displayed overlap.

Target Volume Creation (Moving Results to Clinic)

Analysis results can be used to generate target (visualization) volumes for both benefits and side-effects. Target volumes can be saved as a mesh or a point (e.g., a centroid with additional information as described above).

In an example embodiment, a target volume is definable by a selected point about which the volume is to be drawn and a volume size. (Angles can further be used to define an orientation of the target volume relative to axes of an anatomical space.) For example, in an example embodiment, the system is configured to identify an average center of mass of a selected plurality of VOAs. For example, the system is configured to provide a user-selectable option, in response to selection of which the system is configured to calculate the average center of mass of a set of VOAs selected by the user. The system is further configured to receive a size information and draw a target volume centered on the calculated average center of mass and that is of the size specified by the user.

In an alternative example embodiment, or as an additional alternative option, instead of an average center of mass of the VOAs, the system finds a respective average score for each of a plurality of voxels, where the average score for a voxel is an average of the scores of the VOAs in which the respective voxel is included. The score of a VOA can be based on, for example, results of a stimulation to which the VOA corresponds, as described above. In an example embodiment, the system selects the voxel having the highest average score as the point about which to draw the target volume. Alternatively, the system finds a cluster of highest average scoring voxels, and selects the center of such a cluster as the point about which to draw the target volume. The user can manually enter a size, which the user might determine based on a general intuitive feel.

In an alternative example embodiment, or as an additional alternative option, the system first removes from consideration those VOAs having a score below a predetermined programmed threshold, or a threshold specified by the user, and then finds the voxel having the highest average score (or center of a cluster of highest scoring voxels) of the remaining VOAs to set as the point about which to draw the target volume.

In an alternative example embodiment, or as an additional alternative option, the system first removes from consideration those VOAs having a score below a predetermined programmed threshold, or a threshold specified by the user, and then finds the average center of mass of the remaining VOAs to set as the point about which to draw the target volume.

In an alternative example embodiment of the present invention, the system is configured to receive user input of a target volume size (e.g., as number of voxels, a radius, or any other suitable specification of size), in accordance with which size specification the system is configured to adjust a score threshold to one that results in removing just enough voxels to provide a volume approximately equal to the specified size. Alternatively, the system is configured to receive user input of a target volume size (e.g., as number of voxels, a radius, or any other suitable specification of size), in accordance with which size specification the system is configured to adjust a score threshold to one that results in removing just enough voxels to ensure that the specified size is not exceeded. Alternatively, the system is configured to receive user input of a target volume size (e.g., as number of voxels, a radius, or any other suitable specification of size), in accordance with which size specification the system is configured to adjust a score threshold to one that results in removing just enough voxels to ensure that the specified size is not undershot. In an example embodiment, these described methods of adjusting a threshold in accordance with a user-specified volume size are provided as user-selectable options.

The threshold value can be a percentage, e.g., a user may require the target volume to encompass voxels that make up 80% of all the scores of the considered voxels. For example, the system is configured to receive user-input specifying a percentage, and to set the threshold such that the combined average scores of the remaining voxels (whose individual average scores meet the threshold) is equal to the specified percentage of the sum of the average scores of all considered voxels. That is, the voxels of the output volume are such that $$\frac{\sum_{i=1}^{n\_output} avg\_score\_of\_voxel_i}{\sum_{j=1}^{n\_input} avg\_score\_of\_voxel_j} = x\ \%,$$

where i is a voxel of the output volume, n_output is the number voxels in the output volume, j is a voxel of one or more of the input volumes, n_input is the number of voxels that are included in at least one of the input volumes, and x is the percentage specified by the user.

Compatibility

In an example embodiment, the system is configured to provide compatibility modes in which to generate and/or analyze VOAs. The system is configured to provide de-featuring in the compatibility modes. For example, data can be scaled down to render the data compatible with third party analysis tools, to allow users to perform analysis from the perspective of the other systems.

In an example compatibility mode, the system turns off the ability to simulate VOAs using multiple independent current or voltage sources, so that only a single source is used for all contacts.

After turning off the relevant features, VOAs can then be generated as if they were done using the hardware and parameters supported by the other systems. Such VOAs can then be applied to a visualization, programming, or analysis tool.

As another example, certain systems allows for leadwire contacts to each be set to either on or off, while other systems allow for leadwire contacts to each be set to a plurality of levels besides for on and off, e.g., 20% power, 30% power, etc. If a user is using a system of the former type, the user can set the Guide and/or analysis modules to a compatibility mode in which contact settings can be set to only on and off, and to lockout features not supported by the used hardware. In an example embodiment, the user is presented with a checklist of features for each of which the user can input whether the feature is supported by the hardware being used.

The above description is intended to be illustrative, and not restrictive. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the following claims.

What is claimed is:

1. An interface device comprising:
a processor;
a user input device; and
a display device;
wherein:
the processor is configured to perform the following in response to user input that is received via the user input device and that is an instruction to change a setting of an implanted stimulation device: update a graphical user interface displayed in the display device to indicate that the instructed change has been effected, without the setting of the implanted stimulation device being changed; and
the interface device is:
communicatively coupled to the implanted stimulation device, and is configured such that the interface device does not instruct the implanted stimulation device to effect the instructed change in response to the user input instruction; and
configured to obtain at least one of upper and lower bounds for the setting, the refraining by the interface device from instructing the implanted stimulation device to effect the user input instructed change being according to a condition that the instructed change is to modify the setting to be at a value that does not meet the at least one of the upper and lower bounds.

2. The interface device of claim 1, further comprising:
a charger configured to charge a battery of the implanted stimulation device, wherein, while an actual battery charge level of the implanted stimulation device is fully charged, the processor is configured to:
display in the display device an indication of a battery charge level that is less than the actual battery charge level; and
responsive to use of the charger to charge the battery of the implanted stimulation device, modify the display to show a gradual increase to the battery charge level.

3. The interface device of claim 1, wherein the interface device is configured for placement in a clinical mode and a programming mode, the refraining by the interface device from instructing the implanted stimulation device to effect the user input instructed change being conditional upon that the interface device is in the clinical mode when the user input instruction is received.

4. The interface device of claim 1, wherein the instructed change is a change to at least one of a pulse width, a current amplitude, a polarity, and a power amplitude of at least one electrode.

5. The interface device of claim 1, wherein the update includes modification to at least one of a battery power indication and a battery life indication of the implanted stimulation device.

6. The interface device of claim 5, wherein the instruction is to increase a power output of the implanted stimulation device, and the update includes decreasing a value of the battery life indication.

7. The interface device of claim 5, wherein the instruction is to increase a power output of the implanted stimulation device, and the update includes modification of the battery life indication to indicate a shorter battery life than indicated prior to the modification.

8. The interface device of claim 1, wherein the update includes modification to a position of a current field relative to a representation of an implanted electrode leadwire.

9. The interface device of claim 8, wherein the instruction is to shift the current field.

10. The interface device of claim 9, wherein the user input device includes a plurality of arrows, selection of each of which is interpreted as a respective instruction to shift the current field in a respective direction.

11. The interface device of claim 1, wherein the implanted stimulation device is an implanted pulse generator (IPG) for an implanted leadwire.

12. An interface device comprising:
a processor;
a user input device; and
a display device;
wherein:
the processor is configured to perform the following in response to user input that is received via the user input device and that is an instruction to change a setting of an implanted stimulation device: update a graphical user interface displayed in the display device to indicate that the instructed change has been effected, without the setting of the implanted stimulation device being changed; and
the interface device is:
communicatively coupled to the implanted stimulation device, and is configured such that the interface device does not instruct the implanted stimulation device to effect the instructed change in response to the user input instruction; and
configured to obtain an indication of at least one non-permitted value for the setting, the refraining by the interface device from instructing the implanted stimulation device to effect the user input instructed change being according to a condition that the instructed change is to modify the setting to be at one of the at least one non-permitted values.

13. The interface device of claim 12, wherein the indication of the at least one non-permitted value for the setting is received from a remote device that includes a user input device via which user input of the indication of the at least one non-permitted value is received.

14. The interface device of claim 12, wherein the indication of the at least one non-permitted value for the setting is received from the implanted stimulation device.

15. An interface device comprising:
a processor;
a user input device; and
a display device;
wherein:
the processor is configured to perform the following in response to user input that is received via the user input device and that is an instruction to change a setting of an implanted stimulation device: update a graphical user interface displayed in the display device to indicate that the instructed change has been effected, without the setting of the implanted stimulation device being changed;
the interface device is communicatively coupled to the implanted stimulation device;
the processor is further configured to, in response to the user input, transmit the instruction to the implanted stimulation device; and
the implanted stimulation device to which the interface device transmits the instruction is one that is configured to:
obtain an indication of at least one non-permitted value for the setting; and
ignore the instruction from the interface device, so that the instructed change is not effected, the ignoring of the instruction being according to a condition that the instructed change is to modify the setting to be at one of the at least one non-permitted values.

16. An interface device comprising:
a processor; and
a display device;
wherein the processor is configured to display in the display device a graphical user interface indicating a battery life of an implanted stimulation device that is capable of delivering an electrical stimulation therapy, the indicated battery life being modified by the processor over time to reflect battery life changes calculated to occur when the implanted stimulation device is set to a first stimulation program, the display being provided while the implanted stimulation device is set at a second stimulation program at which the changes are not calculated to occur, wherein, when the battery life is calculated to be low, the processor is configured to output a warning indicating that battery life is below a threshold at which a recharge is recommended.

17. The interface device of claim 16, wherein the interface device includes a charger for charging the implanted stimulation device, and is configured to display output indicating a gradual recharge of the implanted stimulation device by the charger while the implanted stimulation device is already fully charged and not being recharged by the charger.

18. An interface device comprising:
a processor;
a user input device; and
a display device;
wherein:
the processor is configured to:
display in the display device on-settings of a first stimulation program of an implanted stimulation device indicating a present application of the first stimulation program throughout a time period during which settings of the implanted stimulation device vary between (a) at least one of the on-settings of the first stimulation program to perform a first stimulation and on-settings of a second stimulation program to perform a second stimulation, and (b) at least one of on-settings of a third stimulation program to perform a third stimulation and an off setting during which the implanted stimulation device does not perform any stimulation; and
receive via the user input device feedback on an effect of stimulation caused by the implanted stimulation device during the time period.

19. The interface device of claim 18, wherein the processor is configured to transmit the feedback to a server.

20. The interface device of claim 18, wherein the settings of the implanted stimulation device is modified based on the feedback.

21. The interface device of claim 18, further comprising:
at least one sensor that detects indicators of at least one of motor skill and cognitive functioning during the time period.

22. The interface device of claim 18, wherein the settings of the implanted stimulation device cycles through at least two stimulation programs and the off setting.

23. A computer-implemented method comprising:
recording, by a computer processor and in a memory device, a time-stamped log of patient-condition information;
recording, by the computer processor, time-stamped information of settings of an implanted stimulation device;

correlating, by the computer processor, different subsets of the time-stamped log of patient-condition information with different ones of the settings based on the time stamps of the log and the time stamps of the information of the settings; and based on the correlation, automatically modifying, by the processor, the settings.

24. The method of claim 23, wherein the time-stamped information of settings is recorded at predetermined intervals.

25. The method of claim 23, wherein respective portions of the time-stamped information of settings are recorded responsive to respective modifications to the settings.

26. A computer-implemented method comprising:

recording, by a computer processor and in a memory device, a time-stamped log of patient-condition information;

recording, by the computer processor, time-stamped information of groups of settings of an implanted stimulation device;

outputting a graph representing changes to one or more patient conditions indicated by the patient-condition information, the graph being presented against a timeline based on the time-stamped log; and outputting identifications of the settings against the timeline based on the time-stamped information, such that different ones of the groups of settings are displayed at different points along the timeline, the different points representing different ones of the time-stamped times.

27. The method of claim 26, wherein the time-stamped information of settings is recorded at predetermined intervals.

28. The method of claim 26, wherein respective portions of the time-stamped information of settings are recorded responsive to respective modifications to the settings.

29. The method of claim 23, further comprising, based on the correlation, outputting, by the processor, a report on effects of the settings on patient condition.

* * * * *